United States Patent
Yahaba et al.

(10) Patent No.: US 9,261,473 B2
(45) Date of Patent: Feb. 16, 2016

(54) NON-DESTRUCTIVE TESTING SYSTEM

(71) Applicants: HONDA MOTOR CO., LTD., Minato-Ku, Tokyo (JP); F-TECH INC., Kuki-Shi, Saitama (JP)

(72) Inventors: Takanori Yahaba, Saitama (JP); Katsuaki Suwa, Nasukarasuyama (JP); Hayato Fukuda, Kuki (JP)

(73) Assignees: Honda Motor Co., Ltd., Tokyo (JP); F-Tech Inc., Saitama (JP)

(*) Notice: Subject to any disclaimer, the term of this patent is extended or adjusted under 35 U.S.C. 154(b) by 567 days.

(21) Appl. No.: 13/710,813

(22) Filed: Dec. 11, 2012

(65) Prior Publication Data

US 2013/0148689 A1   Jun. 13, 2013

(30) Foreign Application Priority Data

Dec. 12, 2011  (JP) .................................. 2011-270975

(51) Int. Cl.
*G01N 21/35* (2014.01)
*G01N 25/72* (2006.01)

(52) U.S. Cl.
CPC ...................................... *G01N 25/72* (2013.01)

(58) Field of Classification Search
CPC .................. G01N 21/35; G01N 21/71; G01N 2005/0077; G01K 7/00
USPC ................... 374/4, 5, 141, 46, 120, 121, 1, 2; 250/338.1, 339.02, 339.03, 339.06, 250/338.03, 339.14, 341.6, 341.8, 339.09, 250/341.1, 363.01, 363.02; 219/148, 136, 219/121.63, 617, 635, 647, 50
See application file for complete search history.

(56) References Cited

U.S. PATENT DOCUMENTS 3,587,298 A * 6/1971 Jacobs ............................ 73/607
4,557,607 A * 12/1985 Busse .................... G01B 11/06
374/121

(Continued)

FOREIGN PATENT DOCUMENTS

CN   102033081 A    4/2011
DE      4203272 A1 *  8/1993   ......... G01N 21/1717

(Continued)

OTHER PUBLICATIONS

Chinese Office Action issued Jun. 26, 2014 in the corresponding CN Patent Application 201210531668.X with the English translation thereof.

(Continued)

*Primary Examiner* — Gail Kaplan Verbitsky
(74) *Attorney, Agent, or Firm* — Carrier Blackman & Associates, P.C.; Joseph P. Carrier; Fulchand P. Shende

(57) ABSTRACT

Non-destructive testing system performs accurate testing as to whether lamination joining portion of different metal materials is in strong joining state by secure metal joining. The system sets a lamination joining portion of different metal materials of a work to a certain position and angle. Laser light in certain waveform is applied to lamination joining portion surface to capture images by infrared camera, and data processing device obtains infrared images. Based on infrared images, Fourier transform is performed on each pixel of infrared images, and phase image is created by console device. Based on created phase image, effectiveness/defectiveness of joining is determined. In this non-destructive testing, whether reflection by vertical wall in vicinity is significant is determined, based on intensity of infrared images obtained immediately after irradiation with laser and angle between laser light optical axis and testing part surface is finely adjusted to obtain infrared images with less noise.

6 Claims, 11 Drawing Sheets
(2 of 11 Drawing Sheet(s) Filed in Color)

(56) References Cited

U.S. PATENT DOCUMENTS

| | | | |
|---|---|---|---|
| 6,295,335 B1 | 9/2001 | Cossard | |
| 8,742,347 B2 * | 6/2014 | Altmann | G01N 1/00 250/332 |
| 8,822,875 B2 * | 9/2014 | Webster et al. | 219/121.11 |
| 8,822,894 B2 * | 9/2014 | Zheng et al. | 250/201.9 |
| 8,837,045 B2 * | 9/2014 | Popescu et al. | 359/385 |
| 2002/0050566 A1 * | 5/2002 | Nilsson et al. | 250/341.6 |
| 2004/0120383 A1 * | 6/2004 | Kennedy et al. | 374/57 |
| 2006/0146340 A1 * | 7/2006 | Szwaykowski et al. | 356/495 |
| 2007/0254490 A1 * | 11/2007 | Jain | 438/736 |
| 2011/0189379 A1 * | 8/2011 | Ortner | G01N 25/72 427/9 |
| 2012/0298870 A1 * | 11/2012 | Louban et al. | 250/341.6 |
| 2015/0104344 A1 * | 4/2015 | Webster et al. | 419/1 |

FOREIGN PATENT DOCUMENTS

| | | | | |
|---|---|---|---|---|
| DE | WO 0011450 A2 * | 3/2000 | | G01N 21/171 |
| DE | 10 2006 057802 A1 | 10/2007 | | |
| DE | 10 2006 048494 A1 | 4/2008 | | |
| DE | 10 2008 030691 A1 | 1/2010 | | |
| JP | 2009-000700 A | 1/2009 | | |
| JP | 2010-513883 A | 4/2010 | | |
| WO | 02/089042 A1 | 11/2002 | | |
| WO | 2008/071204 A1 | 6/2008 | | |

OTHER PUBLICATIONS

English translation of German Search Report issued in corresponding German Patent Application 10 2012 222 933.7.

* cited by examiner

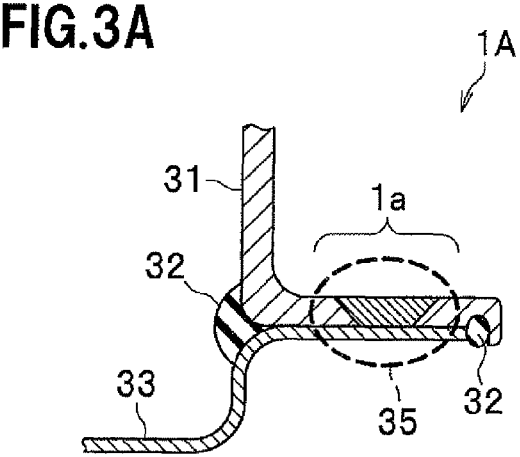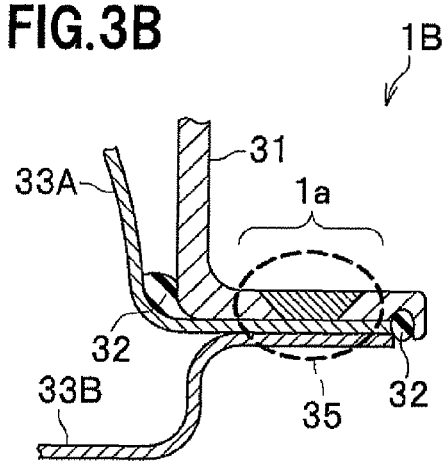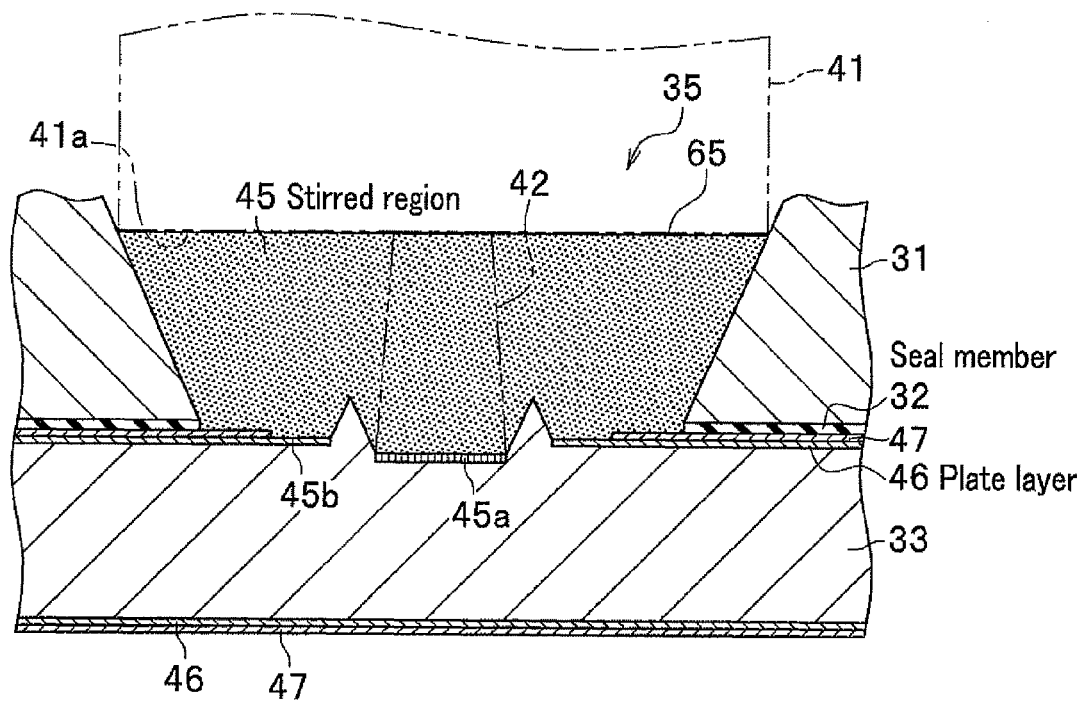

Setting to change surface angle of testing part

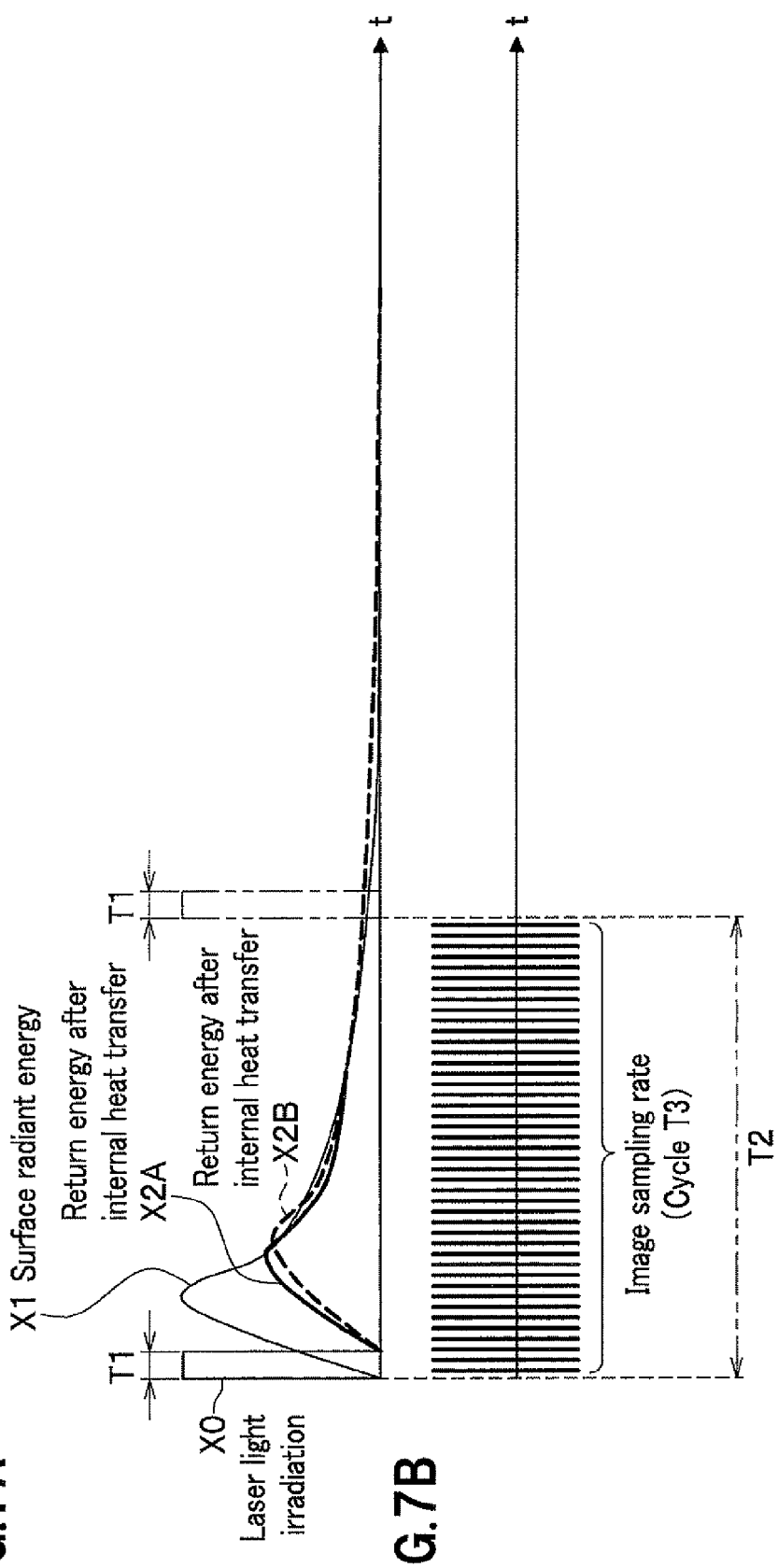

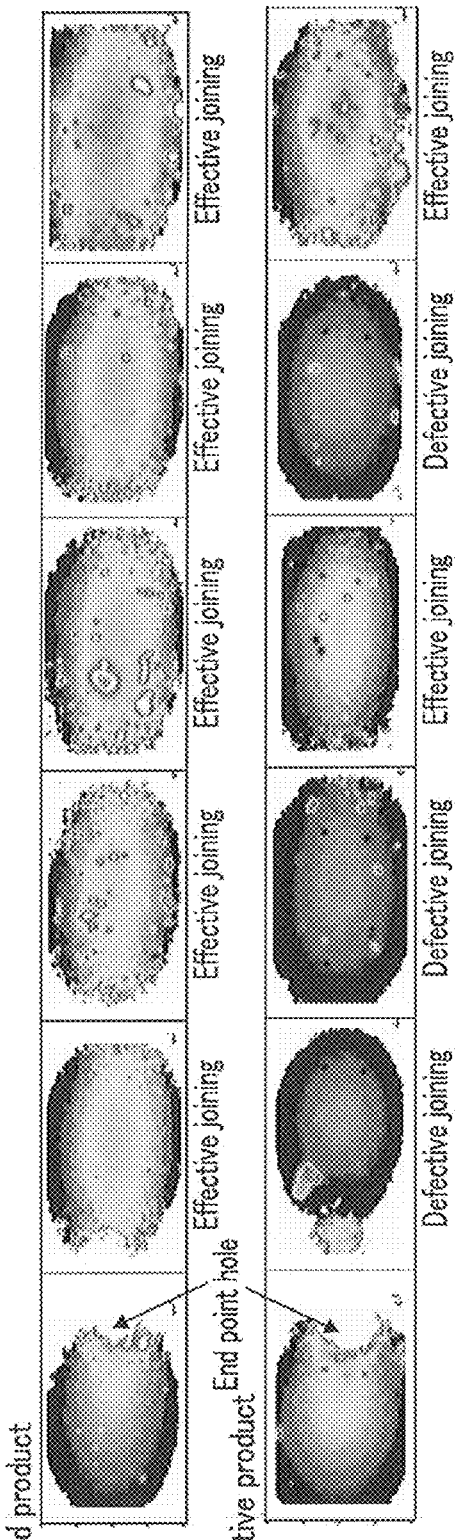

NON-DESTRUCTIVE TESTING SYSTEM

CROSS REFERENCE TO RELATED APPLICATION

This application claims the priority of Japanese Patent Application No. 2011-270975, filed on Dec. 12, 2011, the entire specification, claims and drawings of which are incorporated herewith by reference.

BACKGROUND OF THE INVENTION

1. Field of the Invention

The present intention relates to a non-destructive testing system, and particularly relates to a non-destructive testing system that performs non-destructive testing of a joining portion (lamination joining portion) formed by joining lamination of different metal materials or the like.

2. Description of the Related Art

Conventionally, there is known a technology for joining different metal materials in lamination, for example, by resistance spot welding, friction stir welding, or the like.

Patent Document 1 (Japanese Patent Application Laid-Open No. 2009-00700) discloses such a joining method and a joint structure of different metal materials.

Further, as a non-destructive testing method, Patent Document 2 (Translation of PCT Application JP-T-2010-513883) discloses a technology in which a melted portion and a non-melted portion enclosing the melted portion of a material joining portion is heated temporally, for example, in a pulse form of a rectangular wave or in a sine waveform with a certain cycle to obtain thermal images (corresponding to 'infrared images' in the present invention) transmitted through the material joining portion, and to detect presence or absence of a melted portion.

Still further, Patent Document 3 (Deutsche Patent Application Laid-Open No. 102008030691A1) discloses a technology for non-destructive testing in which the thickness of foreign matter present inside a testing object is detected by infrared lock-in thermography and a technology for a non-destructive testing apparatus using the technology for non-destructive testing. Patent Document 3 also discloses that the thickness of a foreign matter can be detected as follows. That is, heating is performed in a rectangular waveform or a sine waveform at different frequencies, and pixels of thermal images (corresponding to 'infrared images' in the present invention) obtained with the certain cycle are subjected to computation so as to obtain phase images for the respective frequencies. The thickness of a foreign matter can be detected, based on the respective phase images.

SUMMARY OF THE INVENTION

For recent vehicles, it is required to join different metal materials, for example, a steel plate and an aluminum alloy plate, for reduction in the weight of a chassis member or the like.

However, there has been established no technology for accurately testing, by non-destructive testing, whether a lamination joining portion of different metal materials is in a strong joining state by secure metal joining.

The present invention has been developed to solve the above described problem, and an object of the invention is to provide a non-destructive testing system for accurately testing in a non-destructive manner whether a lamination joining portion of different metal materials is in a strong joining state by secure metal joining.

A first aspect of the present invention provides a non-destructive testing system using a non-destructive testing method by infrared lock-in thermography, wherein the non-destructive testing method:

performs heating of a surface on one side of a lamination joining portion of different metal materials from a heating light irradiation source, the heating being in a certain preset waveform;

obtains infrared images from radiant energy from the surface on the one side, the radiant energy being caused by the heating in the certain waveform, the infrared images being obtained with a certain cycle by an infrared camera, obtains an amount and a phase of infrared light by computation processing, based on brightness of each unit pixel of the obtained infrared images; and determines whether joining of the different metal materials is effective or defective, the non-destructive testing system comprising:

a testing object handling device that transports and grips a testing object;

a testing position control unit that controls the testing object handling device and thereby sets the surface of the lamination joining portion of the testing object to certain positions and certain directions respectively relative to the heating light irradiation source and the infrared camera;

a heating control unit that controls irradiation of heating light from the heating light irradiation source;

an infrared image obtaining unit that obtains the infrared images obtained by the infrared camera, based on heating in the certain preset waveform from the heating control unit;

a phase image obtaining unit that obtains an amount and a phase of infrared light by computation processing, based on brightness of each unit pixel of the obtained infrared images, and further creates a phase image; and an effectiveness/defectiveness determining unit that, based on the obtained phase image, determines whether or not a region with a phase delay larger than a certain preset determination value is present in the lamination joining portion, wherein when infrared intensity of an infrared image obtained in an initial period of the heating out of the infrared images obtained, based on the heating in the certain preset waveform, by the infrared image obtaining unit via the infrared camera exceeds a predetermined intensity threshold, the testing position control unit adjusts the direction of the lamination joining portion while maintaining the certain positions of the surface of the lamination joining portion respectively relative to the heating light irradiation source and the infrared camera, and thereafter, the heating control unit again irradiates with the heating light so that the infrared image obtaining unit again obtains infrared images.

According to the first aspect of the invention, the testing object handling device can set the position and the direction of the surface of the lamination joining portion of the testing object by the testing position control unit so that certain same conditions can be obtained in obtaining infrared images by irradiation with heating light from the heating light irradiating source and the infrared camera. Consequently, the infrared camera can obtain infrared images which can be used for non-destructive testing by infrared lock-in thermography with high accuracy.

Further, the phase image obtaining unit performs computation of the temporal transition of the brightness of each unit pixel of the infrared images obtained by the infrared camera, and a phase image with high accuracy can be thereby obtained, which enables easy determination on effectiveness/defectiveness of the joining.

Still further, the infrared image obtaining unit obtains the infrared images via the infrared camera based on the heating in the certain preset waveform, and when the infrared intensity of an infrared image obtained in the initial period of the heating out of the infrared images exceeds a predetermined intensity threshold, the testing position control unit adjusts the directions of the lamination joining portion while maintaining the certain relative positions of the surface of the lamination joining portion respectively relative to the heating light irradiating source and the infrared camera. Thereafter, the heating control unit again irradiates with the heating light so that the infrared image obtaining unit newly obtains infrared images. Accordingly, a non-destructive testing is provided even in such a case that a noise affects the accuracy of an infrared image. That is, for example, there is a case that a vertical wall is present in the vicinity of the lamination joining portion. In this case, a heating light from the heating light irradiating source diffusely is reflected by the surface of the lamination joining portion, and then the reflected light is further reflected by the vertical wall in the vicinity of the lamination joining portion of the testing object, and the heating light from the vertical wall enters the infrared camera. In addition, there may be a case that a heating light from the heating light irradiating source hit on the surface on the one side of the lamination joining portion is reflected by the vertical wall and enters the surface on the one side of the lamination joining portion, and thereafter enters the infrared camera as radiant energy from the surface on the one side. The non-destructive testing is provided with reduction of such a noise on the infrared image.

A second aspect of the present invention provides the non-destructive testing system based on the first aspect, wherein the testing object has a structure having a vertical wall in a vicinity of the lamination joining portion and a possibility that the radiant energy from the surface on the one side of the lamination joining portion reflects on the vertical wall to thereby enter the infrared camera, the radiant energy having been caused by the heating of the surface on the one side of the lamination joining portion by the heating light irradiating source.

According to the second aspect of the invention, it is avoidable that an infrared image obtained by the infrared camera contains as a noise the radiant energy, which is from the heated surface on the one side and is reflected by the vertical wall. This provides a highly accurate phase image even in case that a vertical wall is present in the vicinity of the lamination joining portion, which enables appropriate determination on effectiveness/defectiveness of the joining.

A third aspect of the present invention provides the non-destructive testing system based on the first aspect, wherein the testing object has a structure having a vertical wall in a vicinity of the lamination joining portion and a possibility that the heating light from the heating light irradiating source onto the surface on the one side of the lamination joining portion reflects on the vertical wall to thereby enter the surface on the one side of the lamination joining portion.

According to the third aspect of the invention, non-destructive testing can be performed, reducing a below-described noise on an infrared image, in case that the noise is generated in such a way that a heating light from the heating light irradiating source applied to the surface on the one side of the lamination joining portion reflects on the vertical wall to thereby enter the surface on the one side of the lamination joining portion, and thereafter enters the infrared camera as radiant energy from the surface on the one side, and the noise affects the accuracy of the infrared image. Consequently, a highly accurate phase image can be obtained even in case that a vertical wall is present in the vicinity of the lamination joining portion, which enables appropriate determination on effectiveness/defectiveness of the joining.

A fourth aspect of the present invention provides the non-destructive testing system based on any one of the first to third aspect, wherein the testing position control unit stores in advance a plurality of testing part scanning programs for adjusting only the certain directions of the surface of the lamination joining portion while maintaining the certain positions, the certain directions and the certain positions being respectively relative to the heating light irradiation source and the infrared camera, wherein when infrared intensity of an infrared image obtained in the initial period of the heating out of the infrared images obtained by the infrared camera, the obtaining being triggered by a timing of heating in the preset waveform, exceeds a predetermined intensity threshold, the testing position control unit switches the plurality of testing part scanning programs stored in advance to thereby adjust only the certain directions of the surface of the lamination joining portion respectively relative to the heating light irradiation source and the infrared camera while maintaining the certain relative positions, and wherein the heating control unit thereafter again irradiates with the heating light so that the infrared image obtaining unit again obtains infrared images.

According to the fourth aspect of the invention, it is possible to easily adjusts only the certain relative directions of the surface of the lamination joining portion while maintaining the certain positions relative to the heating light irradiation source and the infrared camera. Thereafter the heating control unit can again irradiate with heating light so that the infrared image obtaining unit can newly obtain infrared images. Accordingly, after knowing that the accuracy of a result of non-destructive testing is insufficient, it is possible to adjust the testing part scanning programs for setting the certain positions and the certain directions of the surface of the lamination joining portion relative to the heating light irradiation source and the infrared camera, and return the testing object to the non-destructive testing process, which enables in advance prevention of a problem of repeating a test and enables non-destructive testing with high accuracy.

According to the present invention, it is possible to provide a non-destructive testing system for accurately testing, in a non-destructive manner, whether a lamination joining portion of different metal materials is in a strong joining state by secure metal joining.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

FIGS. 3A and 3B are illustrations of examples of cross-sections of lamination joining portions of different metal materials of testing objects, wherein FIG. 3A is an illustration of an example of a cross-section of the lamination joining portion of different metal materials formed by friction stir welding of flange portions of an aluminum alloy and a coated double-side plated steel plate after disposing a seal member therebetween, and FIG. 3B is an illustration of an example of a cross-section of the lamination joining portion of different metal materials formed by friction stir welding of flange portions of an aluminum alloy and two coated double-side plated steel plates after disposing a seal member therebetween;

FIG. 4 is an illustration of a cross-section of the lamination joining portion of different metal materials formed by friction stir welding;

FIGS. 6A and 6B are illustrations of adjusting an angle at which laser light is applied to the surface of the lamination joining portion of a testing object, wherein FIG. 6A is an illustration of entrance, into an infrared camera, of a light having reflected on a vertical wall, and FIG. 6B is a conceptual illustration of changing the setting of the surface angle of the lamination joining portion of a testing object in order to prevent the light having reflected on the vertical wall from entering the infrared camera;

FIGS. 7A and 7B are illustrations of the principle of infrared lock-in thermography in which laser light is applied to the surface of a lamination joining portion to obtain the temporal change in the radiant energy radiated from the surface from infrared images, wherein FIG. 7A is an illustration of laser light irradiation, radiant energy (surface radiant energy) caused by heating a surface portion with the laser light, and generation of phase difference due to difference in the thermal conductivity of radiant energy (returning energy after internal heat transfer) that is radiated by the heat, due to the laser light, having returned to the surface after having transferred to the inside, and FIG. 7B is a time chart showing timings of laser light irradiation and timings of sampling infrared images;

FIGS. 10A and 10B are schematic illustrations of application of laser light to the surface of a lamination joining portion formed by friction stir welding and obtaining infrared images, wherein FIG. 10A is a schematic illustration of the lamination joining portion viewed from a right angle side direction with respect to the longitudinal direction of the lamination joining portion, and FIG. 10B is a schematic lustration of moving an irradiated portion onto which laser light is applied for non-destructive testing wherein the surface of the lamination joining portion is viewed from the above;

FIGS. 11A and 11B are illustrations of examples of determining effectiveness/defectiveness of joining by phase images, wherein FIG. 11A is an illustration of examples of phase images of testing objects on which determination of effective joining has been made (effective products), and FIG. 11B is an illustration of examples of phase images of testing objects on which determination of defective joining has been made (defective products); and FIGS. 12A and 12B are illustrations of examples of determining effectiveness/defectiveness of lamination joining portions by phase images in a different manner, wherein FIG. 12A shows an example in case of determining effective joining, the upper section being a plan-view photograph of the cut surface at a joining boundary on which effective joining has been confirmed, the middle section being an illustration of an example of a phase image in case of effective joining, and the lower section being an illustration of an example of phase difference in a phase image of a lamination joining portion in the plan lateral direction, for example, at the center, and FIG. 12B shows an example in case of determining defective joining, the upper section being a plan photograph of the cut surface at a joining boundary on which defective joining has been confirmed, the middle section being an illustration of an example of a phase image in case of defective joining, and the lower section being an illustration of an example of phase difference in a phase image of a lamination joining portion in the plan lateral direction, for example, substantially at the center.

DETAILED DESCRIPTION OF THE PREFERRED EMBODIMENT

Figure 1:
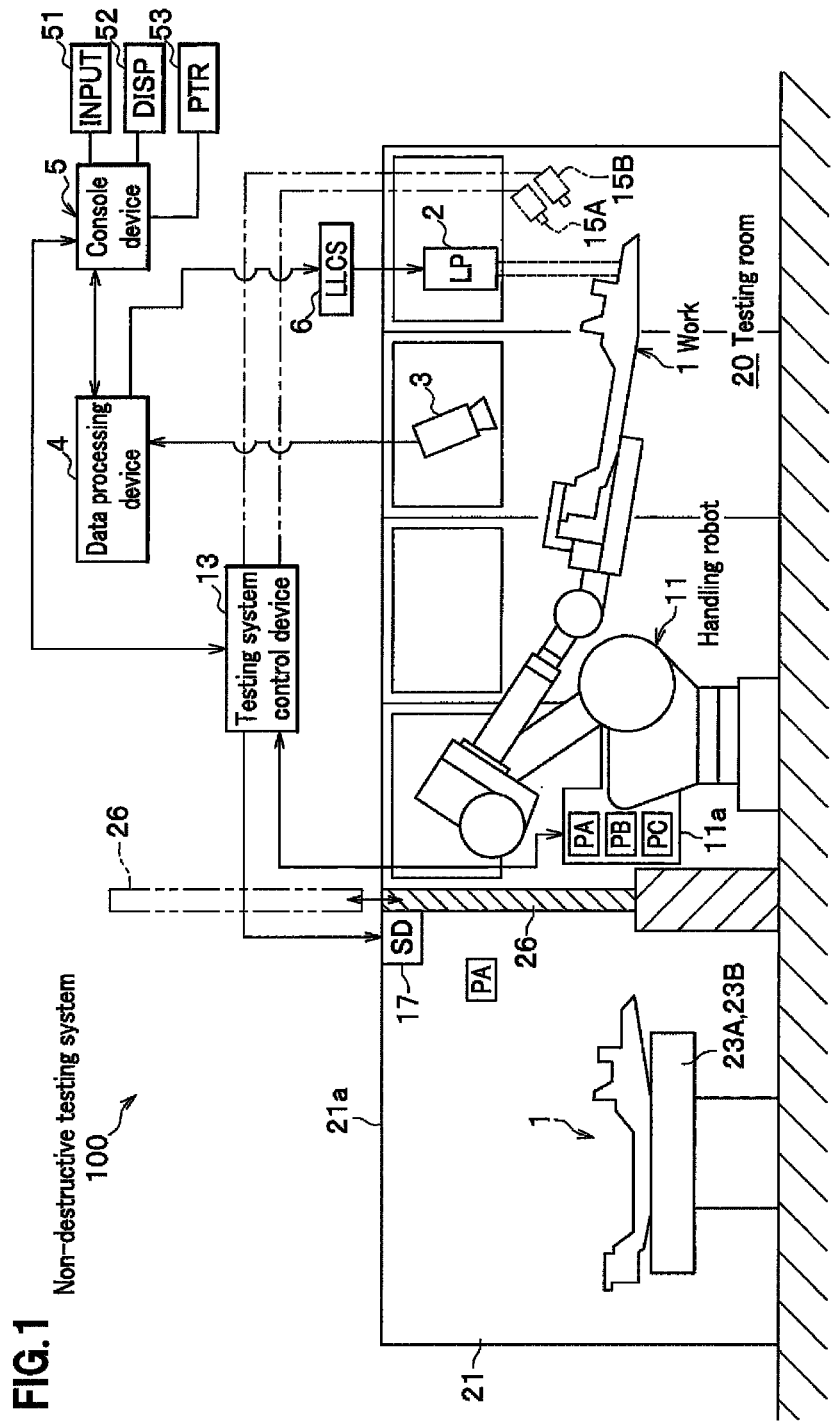
FIG. 1 is a block configuration diagram showing the overview of an entire non-destructive testing system and a schematic side view of the inside of a testing room and the like for testing a testing object handled by the non-destructive testing system.

A non-destructive testing system 100 in the present embodiment will be described below in detail, referring to the drawings.

Figure 2:
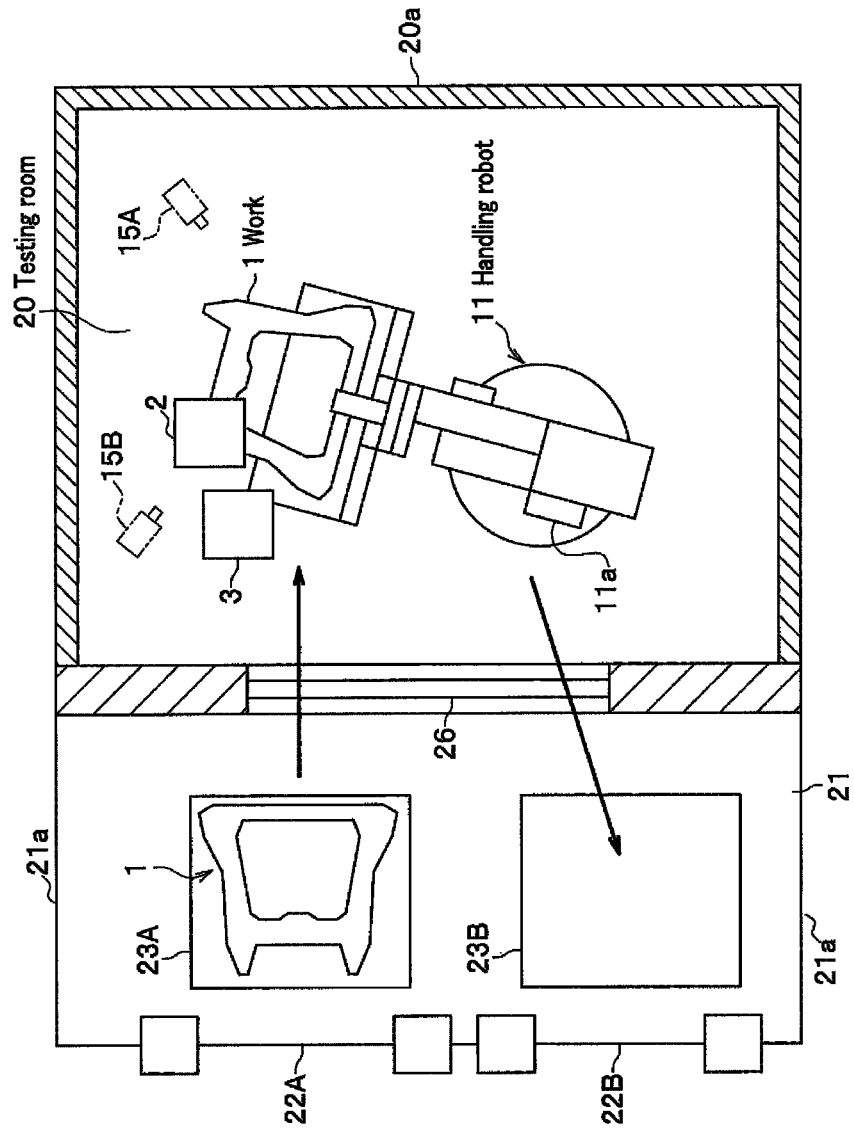
FIG. 2 is an example of a plan view of the disposition inside the testing room shown in FIG. 1.

FIG. 1 is a block configuration diagram showing the overview of an entire non-destructive testing system and a schematic side view of the inside of a testing room and the like for testing a testing object handled by the non-destructive testing system. FIG. 2 is an example of a plan view of the disposition inside the testing room shown in FIG. 1. Herein, FIG. 1 is not associated with the plan view of disposition in FIG. 2, and shows things seen along the circumferential direction, in a view moving with a turn in the left direction in the testing room 20 in FIG. 2.

As shown in FIG. 1, the non-destructive testing system 100 includes a handling robot (a testing object handling device) 11 for handling a work (a testing object) 1, which is a testing object, is installed, and a laser light irradiation section (heating irradiation source) 2 and an infrared camera 3 arranged in the upper portion of the testing room 20 enclosed by a wall 20a (see FIG. 2) and a ceiling. The positions of the laser light irradiation section 2 and the infrared camera 3 are fixed. The position of the handling robot 11 is set such as to be able to obtain infrared images in such a manner that, for example, a spot of laser light of parallel beams hits the surface of respective testing portions of a testing part of a lamination joining portion 35 (see FIG. 5) of the work 1, at certain preset distances and in certain directions from the light irradiation exit of the laser light irradiation section 2 and the lens of the infrared camera 3.

Incidentally, the number of linear testing parts is not limited to one for one work 1, and a testing part often exists at plural positions. Further, the shape of a linear testing part is not necessarily limited to a straight linear shape, and may be a curved shape.

A method of non-destructive testing of one testing part will be described below for simple description.

The handling robot 11 is a multi-joint robot having a grip section, not shown, for gripping a work 1, and includes a controller 11a that controls gripping and releasing by the gripping section, controls setting of the surface of each testing portion of the above-described testing part to the certain preset distance and angle (certain positions and directions) relative to the laser light irradiation section 2 and the infrared camera 3, and also performs other controls.

In order to control the setting of the surface of each testing portion of the above described testing part to the certain preset distance and the certain angle, the handling robot 11 controls the position of the work 1 and the gripping angle, while gripping a certain gripping portion of the work 1, based on, for example, a series of task instructions having been input to the controller 11a in advance.

The reason for controlling the setting of the surface of each testing portion of a testing part to certain distances and certain angles relative to the laser light irradiation section 2 and the infrared camera 3 is to maintain the entrance heat amount through the surface of the each testing portion of the testing part by laser light to be a predetermined constant value, and to enable accurate determination of effectiveness/defectiveness of joining from the temporal transition of radial energy, due to the heat entrance, radiated from the surface of the each testing portion of the testing part.

A testing object delivery room 21 is provided adjacent to the testing room 20, and the testing room 20 and the testing object delivery room 21 can be partitioned by a shutter driving section 17, for example, with a movable shutter 26 that is driven upward/downward and used for light shielding. During testing of the work 1, the shutter 26 is closed so that disturbance of infrared light is prevented from entering the infrared camera 3.

The ceiling and the periphery of the testing object delivery room 21 are enclosed by an outer plate 21a, except a receiving entrance door section 22A (see FIG. 2) and a discharging exit door section 22B (see FIG. 2). The receiving entrance door section 22A and the discharging exit door section 22B can be opened and closed. In the testing object delivery room 21, there are disposed a testing object receiving table 23A for mounting a work 1 to be subjected to the next testing and a testing object discharging table 23B for mounting a work 1 on which testing has been completed. A work 1 to be subjected to the next testing is transported by a transporting device, not shown, to the testing object receiving table 23A and mounted on it, and a work 1 having been tested is carried out from the testing object discharging table 23B.

As shown in FIG. 1, the controller 11a is connected for communication with a testing system control device 13 that integrally controls the non-destructive testing system 100. Further, the testing system control device 13 is connected for communication also with a console device 5 by a communication line, and also controls driving of the shutter driving section 17 to operate the shutter 26 to move it up and down.

Based on a series of task instructions having been input in advance to the controller 11a, the testing system control device 13 instructs the handling robot 11 via the controller 11a to grip the certain gripping portion of a work 1. Then, based on the series of task instructions having been input in advance, the testing system control device 13 controls the handling robot 11 via the controller 11a to repeat a testing task on a series of testing portions from the start point to the end point of a testing part in a preset sequence such as 'fix the positions and angles (directions) of a certain testing portion of a testing part respectively relative to the laser light irradiation section 2 and the infrared camera 3' to 'move the testing part to the next testing portion by a certain amount of movement' to 'fix the positions and the angles of the next testing portion of the testing part relative to the laser light irradiation section 2 and the infrared camera 3 and perform testing'.

A series of task instructions (program) to control the handling robot 11 via the controller 11a to repeat a testing task on a series of testing portions from the start point to the end point of a testing part are input in the controller 11a in advance at least in three kinds, wherein the testing task is such as 'fix the positions and angles (directions) of a certain testing portion of each testing part respectively relative to the laser light irradiation section 2 and the infrared camera 3' to 'move the testing part to the next testing portion by a certain amount of movement' to 'fix the positions and the angles of the next testing portion of the testing part relative to the laser light irradiation section 2 and the infrared camera 3 and perform testing'.

These three kinds of series of task instructions are implemented by (1) a program PA for execution of the testing task on a series of testing portions from the start point to the end point of a testing part such as described above, in a state that, while the certain preset distances of the surface of the respective testing portions of the testing part respectively relative to the laser light irradiation section 2 and the infrared camera 3 are maintained to be the certain preset distances, the angle between the optical axis of laser light and the surface of the respective testing portions of the testing part is a right angle (a reference angle, indicated as '0°' in FIG. 6B), for example, in a view along the moving direction of the testing part, (2) a program PB for execution of the testing task on a series of testing portions from the start point to the end point of a testing part such as described above, in a state that the above-described angle is changed by a certain angle, for example, +2° from the reference angle (indicated as '0°' in FIG. 6B) in a view along the moving direction of the testing part, and (3) a program PC for execution of the testing task on a series of testing portions from the start point to the end point of a testing part such as described above, in a state that the above-described angle is changed by a certain degree, for example, −2°.

As descried later, it will be here assumed that the testing system control device 13 applies first the program PA to the controller 11a to irradiate the respective testing portions of the testing part with laser light and thereby obtain infrared images. Herein, if the total infrared intensity (brightness) of initial or early infrared images having been obtained immediately after irradiation of the surfaces at the respective testing portions of the testing part with the spot of laser light, the infrared images having been obtained by a data processing device 4, exceeds a predetermined intensity threshold (brightness threshold), this fact is notified from the data processing device 4 via a communication line to the controller 11a, and the controller 11a is controlled to return to the start point of the testing part and newly obtain infrared images by irradiating the testing part with laser light by the program PB or the program PC. The details of this control will be described later, referring to the later described flowcharts in FIG. 8 and FIG. 9.

Herein, the programs PA, PB, and PC correspond to the 'testing part scanning programs' in the description of the fourth aspect of the invention.

When testing of the testing part of the work 1 on the testing object receiving table 23A is completed, the testing system control device 13 controls the shutter driving section 17 to open the shutter 26, controls the handling robot 11 to mount the work 1 for which testing having been completed onto the testing object discharging table 23B and take in a new testing work 1 from the testing object receiving table 23A into the testing room 20, and controls the shutter driving section 17 to close the shutter 26.

The testing system control device 13 is, for example, a control computer having an image processing function. A program for integral control of the non-destructive testing system 100 is stored in advance in the storage device of the control computer so that a function to integrally control the testing system control device 13 is realized by executing the program.

Herein, the testing system control device 13 and the controller 11a configure 'the testing position control unit' in the description of the first aspect of the invention.

The laser light irradiation section 2 is connected with a laser light control section (heating control unit) 6 that controls an intensity of laser light irradiated by the laser light irradiation section 2 to be in a certain waveform, for example, a rectangular wave pulse form, a stepped rectangular waveform, a sine waveform, or a triangle waveform, wherein the laser light control section 6 is controlled by the data processing device 4.

A certain waveform of a laser light intensity controlled by the laser light control section 6 corresponds to 'a certain preset waveform' in the description of the first aspect of the invention. This certain waveform of laser light intensity is set to be appropriate for using radiant energy (return energy after internal heat transfer) to appropriately determine effectiveness/defectiveness of joining, wherein the radiant energy is radiated by the heat, caused by heating laser light, that has passed through the boundary portion between the different metal materials at the lamination joining portion 35, based on at least the kinds and the thicknesses of different metal materials at a lamination joining portion 35, thereby deeply transferred, and thereafter returned to the surface on the heating side. The above-described certain waveform can be easily set, for example, by that a test engineer in charge of quality assurance carries out a trial experiment in advance before starting testing.

The certain waveform refers to a waveform optional regarding the height of a waveform (laser light intensity), a waveform duration, and a waveform shape, such as a rectangular pulse form as described above, a stepped increase/decrease rectangular waveform that increases in a step form and then decreases, a sine waveform, a triangle waveform, a trapezoid waveform, and other waveforms. This certain waveform of the laser light intensity is set by input to the console device 5 by the test engineer, using a later-described input section 51 (see FIG. 5).

The data processing device 4 is connected for communication with the console device 5 and the testing system control device 13 by communication lines. The console device 5 includes the input section 51 including an input device such as a mouse and a keyboard, a display section 52 such as a liquid crystal display device, an output section 53 configured with a printer device capable of color printing, and the like.

The functions of the data processing device 4 and the console device 5 will be described later in details in the description of FIG. 5.

The lamination joining portion 35, which is the testing part of the work 1, will be described below, referring to FIGS. 3A, 3B and FIG. 4. FIGS. 3A and 3B are illustrations of examples of the cross-sections of the lamination joining portions of different metal materials of testing objects, wherein FIG. 3A is an illustration of an example of the cross-section of the lamination joining portion of different metal materials formed by friction stir welding of flange portions of an aluminum alloy and a coated double-side plated steel plate after disposing a seal member therebetween, and FIG. 3B is an illustration of an example of the cross-section of the lamination joining portion of different metal materials formed by friction stir welding of flange portions of an aluminum alloy and two coated double-side plated steel plates after disposing a seal member therebetween.

The lamination joining portion 35 of a work 1A shown in FIG. 3A, the work 1A being a chassis member of a vehicle, is an example in which an aluminum alloy member 31, which is a die-cast member of aluminum alloy, and a steel plate 33 are joined with each other by friction stirring with a seal member 32 therebetween at a flange portion 1a. Herein, the steel plate 33 is, for example, first zinc-plated on both surfaces thereof for anti-corrosion and is further coated by electrode position on the outer sides of the surfaces, though not shown in the figure. Incidentally, the reason for sandwiching the seal member 32 between the aluminum alloy member 31 and the steel plate 33 of the flange portion 1a is to form a water sealing structure for prevention of entrance of water and the like and to prevent electrical corrosion.

The lamination joining portion 35 of a work 1B shown in FIG. 3B, the work 1B being a chassis member of a vehicle, is an example in which an aluminum alloy member 31, which is a die-cast member of aluminum alloy, and lamination of two steel plates 33A, 33B are joined with each other by friction stirring with a seal member 32 therebetween at a flange portion 1a. A seal member 32 is not arranged between the steel plate 33A and the steel plate 33B because the two steel plates are of the same kind of metal.

FIG. 4 is an illustration of a cross-section of the lamination joining portion of different metal materials formed by friction stir welding. Herein, FIG. 4 shows the lamination joining portion 35 shown in FIG. 3A as an example, wherein a region stirred by a probe 42 and a shoulder 41a of a tool and thereby composition-fluidized is shown as a stirred region 45; and a portion, where metal joining has been made in such a manner that the main body portions of the aluminum alloy member 31 and the steel plate 33 have been stirred at the position of the probe 42, is shown as a joining boundary surface 45a.

A tool used for applying a friction stir welding method to lamination joining is, for example, as shown in FIG. 4, has a probe 42 at the tip end of a tip end portion 41 in a cylindrical shape, and is provided with a shoulder 41a on the lower outer circumferential side of the tip end portion 41. While being rotated, the tool is pressed onto the different metal materials side, and the tool is horizontally moved along the flange portion 1a (see FIG. 3) so that the lamination joining portion 35 (see FIG. 3) is formed in a desired length on a line by the friction stir welding method.

The shape of the probe 42 of the cylindrical tip end portion 41 of the tool is appropriately selected, depending on the kinds and thicknesses of the different metal materials to be joined in lamination.

A metal bonding boundary surface is formed at the joining boundary surface 45a, and the different metal materials are joined with each other with a large strength. Incidentally, even in case that an intermetallic compound is formed at the joining boundary surface 45a, the different metal materials are joined with each other by a large strength.

On both sides of the joining boundary surface 45a in the stirred region 45, a shoulder portion 45b is formed by that the tip end portion 41 abuts and stirs the steel plate 31 with contact therebetween at the time of friction stir welding, wherein a plate layer 46 and a coating material 47 by electrode position coating remain. Accordingly, the aluminum alloy member 31 and the steel plate 33 are not joined at the shoulder portion 45b.

Incidentally, regarding the joining boundary surface 45a and the shoulder portion 45b on the lower end side of the stirred region 45, it is at least required that the seal member 32 is absent at the joining boundary surface 45a which is pushed outside, and preferably, the seal member 32 is absent on both regions, and the joining boundary surface 45a and the shoulder portion 45b are pushed outside.

On the surface side of the stirred region 45, formed is a surface signature 65 having a color, luster, and the like which are different from those of the surfaces of portions other than the lamination joining portion 35 of the aluminum alloy member 31.

Data Processing Device 4

The data processing device 4 and the console device 5 will be described below in detail, referring to FIGS. 5 to 7B. FIG. 5 is a detail Nock configuration diagram of the non-destructive testing data processing device in FIG. 1, the non-destructive testing data processing device using an infrared lock-in thermography. FIGS. 6A and 6B are illustrations of adjusting an angle at which laser light is applied to the surface of the lamination joining portion of a testing object, wherein FIG. 6A is an illustration of entrance of a light having reflected on a vertical wall into an infrared camera, and FIG. 6B is a conceptual illustration of changing the setting of the surface angle of the lamination joining portion of a testing object in order to prevent the light having reflected on the vertical wall from entering the infrared camera. FIGS. 7A and 7B are illustrations of the principle of infrared lock-in thermography in which laser light is applied to the surface of a lamination joining portion to obtain the temporal change in the radiant energy radiated from the surface by infrared images, wherein FIG. 7A is an illustration of laser light irradiation, radiant energy (surface radiant energy) caused by heating a surface portion with laser light, and generation of phase difference due to a difference in the thermal conductivity of radiant energy (returning energy after internal heat transfer) that is radiated from the surface by the heat of laser light having returned to the surface after having been transferred to the inside and, and FIG. 7B is a time chart showing timings of laser light irradiation and timings of sampling infrared images. In FIG. 7A, the waveform of the laser light is shown as a rectangular waveform as an example, however, can be set as appropriate.

Figure 5:
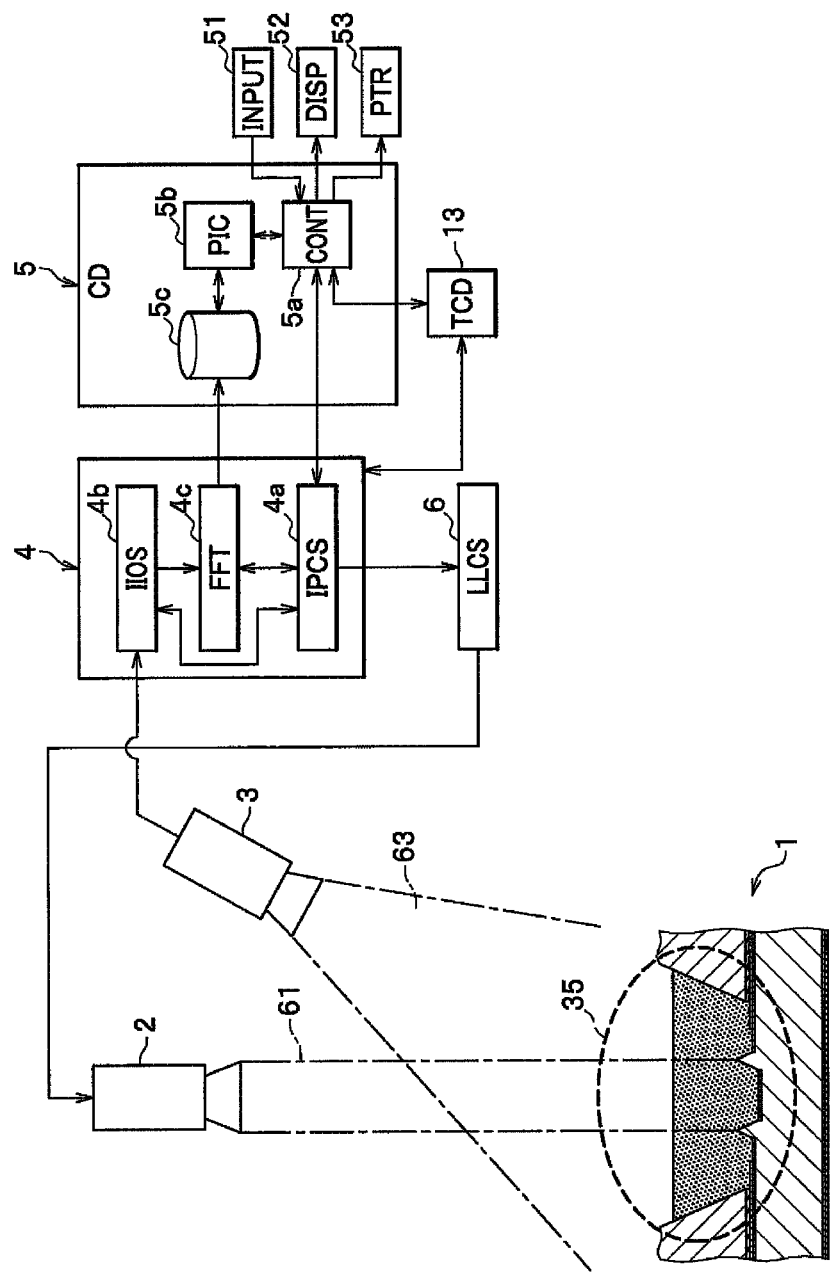
FIG. 5 is a detail block configuration diagram of the non-destructive testing data processing device in FIG. 1, the non-destructive testing data processing device using an infrared lock-in thermography.
Figure 6A:
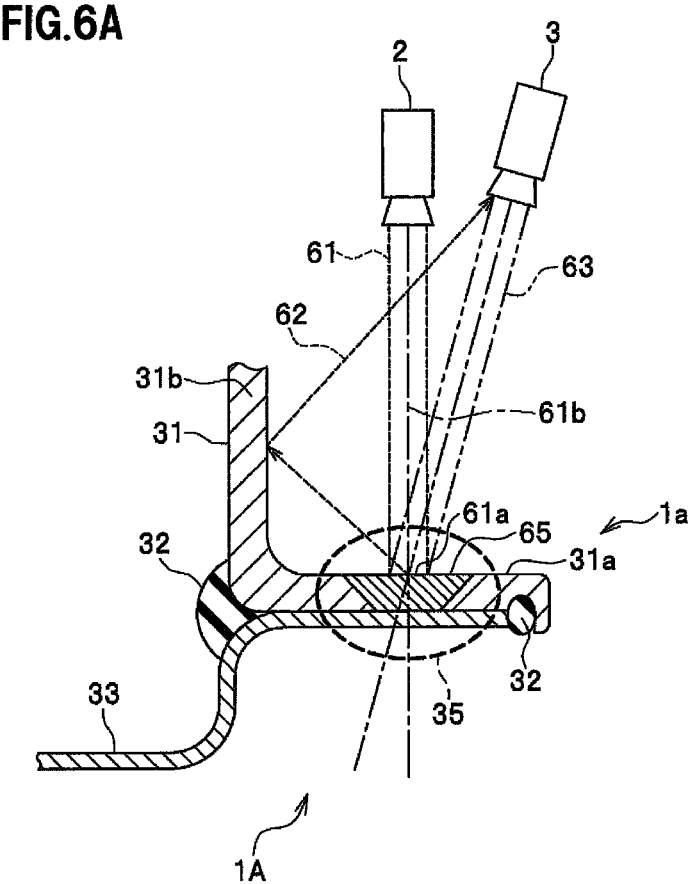
Figure 6B:
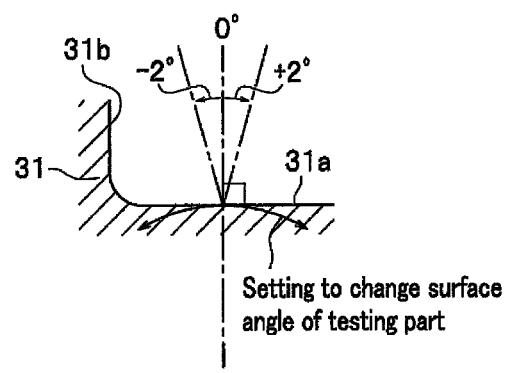

The data processing device 4 is an image processing computer dedicated to image processing functions, and, as shown in FIG. 5, the data processing device 4 includes an image processing control section (heating control unit) 4a (IPCS 4a), an image obtaining section (infrared image obtaining section) 4b (IIOS 4b), and a fast Fourier transform section (phase image obtaining unit) 4c (FFT 4c). The image obtaining section 4b includes a memory that is, for example, capable of storing a large number of infrared images and appropriate for fast input/output.

The console device 5 (CD 5) is a personal computer or an engineering computer, and as function sections, includes a control section (effectiveness/defectiveness determination unit) 5a (CONT 5a), a phase image computing section (phase image obtaining unit) 5b (PIC 5b), and a storage section (phase image obtaining unit) 5c, and also includes the input section (INPUT) 51, such as a keyboard and a mouse, the display section 52 (DISP 52), such as a color liquid crystal display device, and the output section 53 (PTR 53), such as a color printer device.

The data processing device 4 is controlled by instructions from the control section 5a of the console device 5.

Upon a heating control instruction, which corresponds to the above-described preset certain waveform, from the control section 5a of the console device 5, the image processing control section 4a controls the laser light control section (LCS) 6 so that the laser light control section 6 controls the laser light irradiation section 2 to output a laser light with an intensity in the certain waveform from the laser light irradiation section 2. Taking an example of a case that a rectangular wave is set as the certain waveform, the laser light control section 6 controls the laser light irradiation section 2 to output the laser light for a certain temporal width T1 (see FIG. 7), upon heating control instruction from the image processing control section 4a.

Further, based on an input of setting a first image obtaining control instruction, from the control section 5a of the console device 5, to set a certain total amount of infrared images to be obtained, the image processing control section 4a inputs, to the image obtaining section 4b, the first image obtaining control instruction to obtain a certain total obtaining number N1 of infrared images with a certain cycle T3 (see FIG. 7), for example, with a cycle of 300 Hz in the period T2, with the above-described heating control instruction of laser light as a trigger signal, and controls the image obtaining section 4b to temporarily store the infrared images in the certain total obtaining number N1 in the memory of the image obtaining section 4b.

Herein, the brightness of each pixel of obtained infrared images in the certain total obtaining number N1 are digitized and these infrared images are temporarily stored in the memory of the image obtaining section 4b. Herein, 'pixel' corresponds to 'unit pixel' in the description of the first aspect of the invention.

Based on an input, from the control section 5a of the console device 5, of setting a second image obtaining control instruction for determination of an initial brightness, the image processing control section 4a reads, from the memory of the image obtaining section 4b, a certain number N1A of infrared images to be obtained in the initial period of the period T2, and computes the average value of the infrared intensities of all the images in the certain number N1A of infrared images to obtain an infrared intensity. Then, the image processing control section 4a compares the intensity threshold and the computed infrared intensity, the intensity threshold having been set in advance by an operator, corresponding to the above-described waveform of laser light and having been input via the console device 5. Thus, the image processing control section 4a determines whether or not the computed infrared intensity of all the images is smaller than the intensity threshold.

If the computed infrared intensity of all the images is smaller than the intensity threshold, the image processing control section 4a determines that infrared images in response to the laser light heating are normally obtained, and based on an input, from the control section 5a of the console device 5, of setting a third image obtaining control instruction for setting the number of infrared images to be used for Fourier transform, the image processing control section 4a inputs an image processing computation instruction to the fast Fourier transform section 4c to read infrared images in a certain number N1B of infrared images after a certain initial time delay ΔT (not shown in FIG. 7) in the period T2 from the memory of the image obtaining section 4b and perform fast Fourier transform.

The certain number N1B of infrared images is the number of infrared images that can be obtained with a cycle T3 during the time by subtracting the certain time delay ΔT from the period T2.

The initial certain number N1A of infrared images in the period T2 are not included in the infrared images in the above-described certain number N1B of infrared images after the initial certain time delay ΔT in the period T2, and are the infrared images initially obtained by the image obtaining section 4b, triggered by the heating control instruction.

The certain cycle T3 is not limited to the specification of the image pickup speed itself of the infrared camera 3, and can be appropriately selected within a range that allows computation processing of the infrared amounts and phases of respective pixels from infrared images in case that the specification of the image pickup speed of the infrared camera 3 is a fast speed.

The certain time delay ΔT and the certain number N1B of infrared images are set to be appropriate for using infrared images to appropriately determine effectiveness/defectiveness of joining, wherein the infrared images are based on radiant energy (return energy after internal heat transfer) radiated by the heat, the heat having been caused by a laser light in the certain waveform, that has passed through the boundary portion between the different metal materials at the lamination joining portion 35, corresponding to at least the kinds and the thicknesses of different metal materials at a lamination joining portion 35, thus deeply transferred, and thereafter returned to the surface on the heating side.

This certain time delay ΔT and this certain number N1B of images can also be easily set, for example, by that a test engineer in charge of quality assurance carries out a trial experiment in advance before starting testing, and can be set through input by the test engineer, using the input section 51 (see FIG. 5) of the console device 5.

The image processing control section 4a controls the image obtaining section 4b and the fast Fourier transform section 4c to perform data processing, assigning an identifier for each testing portion of the testing part of the work 1.

If the computed infrared intensity of all the images is larger than or equal to the intensity threshold, the image processing control section 4a determines that infrared images in response to the laser light heating are not normally obtained, and controls the fast Fourier transform section 4c to halt short-time fast Fourier transform of the infrared images in the certain number N1B of infrared images out of the certain number N1 of infrared images temporarily stored in the memory of the image obtaining section 4b, and controls the image obtaining section 4b to delete the infrared image data of the certain total number N1 of infrared images.

Further, the image processing control section 4a transmits a signal, via a communication line to the testing system control device 13 (TCD 13), notifying that testing carried out by then from the start point to the end point of the testing part is inappropriate so that the testing system control device 13 controls the controller 11a to switch a series of task instructions (program), for example, from the standard program PA to the program PB, wherein a series of task instructions (program) instructs the handling robot 11 via the controller 11a to repeat a testing task on a series of testing portions from the start point to the end point of a testing part such as 'fix the positions and the angles (directions) of a certain testing portion of the current testing part respectively relative to the laser light irradiation section 2 and the infrared camera 3' to 'move the testing part to the next testing portion by a certain amount of movement' to 'fix the positions and the angles of the next testing portion of the testing part relative to the laser light irradiation section 2 and the infrared camera 3 and perform testing'. If a program currently used for the testing part is, for example, the program PB, control is performed to switch the program PB to the program PC.

The fast Fourier transform section 4c receives an image processing computation instruction that is input after the image processing control section 4a has determined that infrared images have been normally obtained, and reads out the above-described certain number N1B of infrared images out of the certain total obtaining number N1 of infrared images temporarily stored in the image obtaining section 4b.

Thereafter, the fast Fourier transform section 4c performs fast Fourier transform computation of the short-time Fourier transform for each pixel of the certain number N1B of infrared images between the certain number N1B of infrared images, and makes a result of the short-tine Fourier transform of the brightness of each pixel be stored in a short-time Fourier transform storage area of the storage section 5c of the console device 5. Then, the fast Fourier transform section 4c notifies via the image processing control section 4a to the control section 5a that the computation of the above-described short-time Fourier transform has been completed. Upon reception of the notification on the completion of computation of the short-time Fourier transform, the image processing control section 4a controls the image obtaining section 4b to delete the temporarily stored infrared images in the certain total obtaining number N1.

That is, the fast Fourier transform section 4c in the present embodiment performs frequency analysis, such as an ordinary short-time Fourier transform, and performs computation processing to perform analysis of the phase (phase of infrared light) with respect to temporal transition of the brightness (amount of infrared light) of each pixel.

The computation processing to perform analysis of phase with respect to the temporal transition of the brightness of each pixel by the fast Fourier transform section 4c corresponds to 'obtains an amount and a phase of infrared light by computation processing, based on brightness of each unit pixel of the obtained infrared images' in the description of the first aspect of the invention.

Thus, computation processing of infrared lock-in thermography on one testing portion of a series of testing portions of the testing part of a testing object is completed.

When the image processing control section 4a has determined as described above that the infrared intensity, as a result of the infrared intensity computation, as an average value of the certain initial number N1A of infrared images in period T2 is larger than or equal to the threshold, the image processing control section 4a transmits a signal via the communication line to the testing system control device 13, the signal notifying that testing from the start point of the testing part to the testing portion of this time is inappropriate. When the testing system control device 13 has received this signal, the testing system control device 13 instructs the console device 5 to delete a series of computation processing results from the start point to the current testing portion of the testing part, the results having already been input from the fast Fourier transform section 4c, and the console device 5 deletes, via the control section 5a and from the storage section 5c, the series of computation results of short-time Fourier transform and phase images from the start point to the current testing portion of the testing part.

Further, in case that a determination of effectiveness/defectiveness of joining has been already partially made on the testing part, based on a phase image, before it is determined that testing from the start point to the current testing portion of the testing part is inappropriate, the result of determination of effectiveness/defectiveness of the joining is also deleted.

Console Device 5

The control section 5a of the console device 5 performs settings of a laser light with a certain waveform intensity to be output from the laser light irradiation section 2 by input via the input section 51. For example, in the example shown in FIG. 7, there are setting of a certain time width T1 and a certain cycle T3 of the laser light of a rectangular waveform intensity, setting of a certain total obtaining number N1 of infrared images (or period T2) that corresponds to the input setting of the above-described first image obtaining control instruction, setting of the timings of the start and completion of obtaining a certain number N1A of infrared images used for initial brightness determination that corresponds to input setting of the above-described second image obtaining control instruction (setting from which image and to which image of the certain total obtaining number N1 of infrared images are to be used), setting an intensity threshold being a determination value, setting of a time delay ΔT and a certain number N1B of infrared images that correspond to input setting of the above-described third image obtaining control instruction, and setting of a specific frequency ω, to which attention is paid, after computation processing of the short-time Fourier transform, and setting the like. The control section 5a has a function to input necessary parameters out of the above-described parameters to the image processing control section 4a of the data processing device 4.

The value of the specific frequency ω to be focused on after computation processing of the short-time Fourier transform is set to be appropriate for using infrared images to appropriately determine effectiveness/defectiveness of joining, wherein the infrared images are based on radiant energy (return energy after internal heat transfer) radiated by the heat, the heat having been caused by a laser light in the certain waveform, that has passed through the boundary portion between the different metal materials at the lamination joining portion 35, corresponding to at least the kinds and the thicknesses of different metal materials at a lamination joining portion 35, thus deeply transferred, and thereafter returned to the surface on the heating side.

Further, upon reception of a notification of completion of the short-time Fourier transform computation from the image processing control section 4a of the data processing device 4, the control section 5a outputs an instruction to the testing system control device 13 to move the work 1 so that a new testing portion of the testing part can be irradiated and heated with laser light. Upon completion of testing of all the testing portions from the start point to the end point of the testing part, the control section 5a inputs a signal notifying the completion of testing of the testing part to the testing system control device 13. Then, the testing system control device 13 checks whether there is a testing part, of the work 1, having not been tested yet, and if there is, the control section 5a instructs the controller 11a and the data processing device 4 to perform testing of the next testing part.

Further, upon reception of a notification of completion of computation of the short-time Fourier transform from the image processing control section 4a of the data processing device 4, the control section 5a outputs an instruction to the phase image computing section 5b to create a phase image, for example, corresponding to the above-described specific frequency ω. Upon reception of the instruction to create a phase image from the control section 5a, the phase image computing section 5b reads out from the storage section 5c a computation result of the short-time Fourier transform of the respective testing portions of the testing part, creates a phase image with reference to a trigger signal of the above-described heating control signal of laser light, and stores the phase image into the phase image storage area of the storage section 5c, assigning an identifier for each testing portion of the testing part of the above-described work 1. The phase image computing section 5b then designates certain colors with certain bandwidths to phase-delayed digital values computed above for the respective pixels of the obtained phase image. The phase image computing section 5b performs image processing so that, corresponding to the order of the magnitude of phase delay from smaller ones to larger ones, the testing portions of a testing part of the work 1 are displayed in the order of colors white, dark red, orange, yellow, yellow-green, green, dark green, blue, and dark blue, then assigns an identifier for each testing portion of the testing part of the work 1, and stores the phase image in the phase image storage area of the storage section 5c.

Then, the control section 5a reads out the phase image in the storage section 5c. Based on a phase delay (a certain determination value) B$_{STD}$ (see FIG. 12) that is a determination criterion having been input in advance via the input section 51, the control section 5a determines effectiveness/defectiveness of joining of different metal materials at the respective testing portions of the testing part, and outputs the determination together with a colored phase image to the output section 53.

FIG. 6A is an illustration of entrance of a reflection laser light 62 of a laser light (heating light) 61 into the infrared camera 3, taking an example of FIG. 3A. The laser light 61 is perpendicularly emitted by the laser light irradiation section 2 onto the surface 31a of the lamination joining portion 35 of the flange portion 1a. When a vertical wall 31b is present in the vicinity of the lamination joining portion 35, a reflection laser light (surface radiant energy shown in FIG. 7A) having diffusely reflected on the surface signature 65 of an irradiated portion 61a reflects on the vertical wall 31b, resulting in that the reflection laser light becomes the reflection laser light 62 that enters the infrared camera 3. In such a case, heat due to the laser light 61 transfers from the surface 31a of the lamination joining portion 35 having been heated by the laser light 61, through inside, down to the lower side of the joining boundary surface 45a (see FIG. 4) of the lamination joining portion 35. Then, radiant energy (the return energy after the internal heat transfer shown in FIG. 7A) radiated by a return of the heat to the surface 31a also reflects on the vertical wall 31b and enters the infrared camera 3 as the reflection laser light 62. That is, a flare phenomenon occurs. As a result, it becomes unable to obtain an infrared image with correct detection of the return energy after the internal heat transfer from the respective tiny portions of the surface 31a of the lamination joining portion 35.

Particularly, in case that the waveform of the irradiation heating with a cycle T2 by the laser light 61 is a sine wave, the component of a surface reflection light (the surface radiant energy shown in FIG. 7A) of the laser light 61, the component directly entering the infrared camera 3; the reflection laser light 62 that is caused by diffused reflection of a surface reflection light on the surface signature 65 of the irradiated portion 61a, hits against and reflects on the vertical wall 31b to thereby enter the infrared camera 3; and the radiant energy (the return energy after the internal heat transfer shown in FIG. 7A) radiated by a return of the heat after having entered and internally transferred, are simultaneously taken in as an infrared image. Then, in the stage of creating a phase image after Fourier transform thereafter, the surface reflection light up to the delayed time ΔT in surface heating by the laser light 61 is removed without causing a problem, however, on the other hand, the effect of the surface radiant energy that reflects on the vertical wall 31b after the delayed time ΔT and enters the laser light irradiation section 2 as the reflection laser light 62 and the effect of the return energy after internal heat transfer remain as noises as they are without accurately representing the surface distribution of the return energy after internal heat transfer.

In FIG. 6A, an example is shown, taking a case that the laser light 61 having entered from the laser light irradiation section 2 into the surface 31a of the lamination joining portion 35 of the flange portion 1a reflects on the vertical wall 31b and enters the infrared camera 3 as the reflection laser light 62, however, a case that an infrared image is not normally obtained is not limited thereto.

If the lamination joining portion 35 of the flange portion 1a is close to the vertical wall 31b, in case that the laser light 61 reflects on the irradiated portion 61a to hit against the lower portion of the vertical wall 31b, then reflects on the vertical wall 31b to enter the surface 31a of the lamination joining portion 35, and thereafter enters the infrared camera 3 as a surface reflection light, it is also recognized that an infrared image is not normally obtained.

This is because, in this case, for example, if the laser light 61 reflects on the vertical wall 31b and thereby enters the surface 31a of the lamination joining portion 35, the surface 31a of the lamination joining portion 35 is not uniformly heated by the laser light 61, and the surface distribution of return energy after internal heat transfer cannot be accurately represented.

Hereinafter, an effect that the surface distribution of return energy after internal heat transfer is not accurately represented and a noise is caused by such a vertical wall 31b in the vicinity of a testing part will be referred to merely as 'noise on an infrared image due to light reflection by a vertical wall in the vicinity of a testing part'.

In this situation, in case that the certain total obtaining number N1 of infrared images are obtained in the certain cycle T3 (see FIG. 8), for example, a cycle of 300 Hz, triggered by a heating control instruction for laser light as a trigger signal, and the above-described infrared intensity computed on the initial certain number N1A of infrared images (not shown in FIG. 7) out of the total obtaining number N1 of infrared images is larger than or equal to the threshold, the image processing control section 4a determines that an infrared image is not normally obtained, recognizing that the reflection laser light 62 from the vertical wall 31b and a reflection light after the laser light 61 reflects on the vertical wall 31b and irradiates the surface 31a of the lamination joining portion 35 make a large amount of entrance of light into the infrared camera 3.

In case such a determination has been made, the testing system control device 13 outputs an instruction to the controller 11a to incline the surface of the testing part of the work 1A by a certain angle, for example, to a side of +2° from the right angle (represented by '0°' in FIG. 6B) when viewed from the moving direction of the testing part, as shown in FIG. 6B, so that reflection from the vertical wall 31b is decreased, and controls the controller 11a to again obtain infrared images of the testing portions of the series from the start point to the end point of the testing part.

The handling robot 11 is a multi-joint robot. If the angle of only one joining portion is changed, although it is easy to change the angle of the optical axis of a laser light 61, when viewed from the moving direction of a testing part, with respect to the surface of the testing part, the distances (positions) of the surface of the testing part relative to the laser light irradiation section 2 and the infrared camera 3 also change. Accordingly, three kinds of programs PA, PB, and PC for testing position control are prepared in advance as described above, the controller 11a switches between these programs, and it is thereby possible to easily obtain an infrared image without a flare and determine effectiveness/defectiveness of accurate joining.

Incidentally, even when the angle viewed from the moving direction of a testing part is changed approximately by ±2° from a right angle, if the relative distances (positions) between the surface of the testing part and the laser light irradiation section 2 and the infrared camera 3 remain the same, the amount of entering heat by the laser light 61 does not significantly change, and a problem is not caused in accurately determining the effectiveness/defectiveness of joining.

In FIG. 7A, for example, a rectangular waveform X0 with a temporal width T1 represents a laser light with an intensity in a rectangular waveform to output from the laser light irradiation section 2. A curve X1 represents the temporal change in radiant energy, by laser light, from the surface portion of a testing portion of the testing part. Heat by the laser light transfers down to the lower side of the joining boundary surface 45a (see FIG. 4) of the lamination joining portion 35 of a work 1, then the heat returns to the surface and radiates radiant energy (return energy after internal heat transfer) whose frequency becomes low as represented by a curve X2A or X2B. Accordingly, in order to detect by an infrared lock-in thermography whether or not the joining boundary surface 45a of the lamination joining portion 35 of the work 1 is normally formed, a specific frequency ω, to which attention is paid, is set for creating a phase image, based on a result of the short-time Fourier transform by the fast Fourier transform section 4c. The specific frequency ω is set, taking into account the heat transfer property corresponding to the different metal materials to be subjected to lamination joining and the thickness of the metal material on the surface side (the side irradiated with laser light). The lower the heat transfer property is and the thicker the metal material on the surface side is, the lower the specific frequency ω is set and the longer the temporal width T1 of a certain waveform is set.

In case that a metal bonding boundary including formation of a intermetallic compound is formed on the joining boundary surface 45a between the aluminum alloy member 31 (see FIG. 4) of the lamination joining portion 35 of the work 1 and the steel plate 33 (see FIG. 4), radiant energy (return energy after internal heat transfer) radiated by a return of heat after internal heat transfer to the same depth is obtained with a relatively small phase delay as represented by the curve X2A. In contrast, in case that a metal bonding boundary including formation of a intermetallic compound is not formed at the joining boundary surface 45a, and friction stir welding is insufficient such that, for example, the seal member 32 (see FIG. 4) remains or a small void, in other words, a small joining defect is caused, it takes time for the surface heat by laser light to deeply transfer to the steel plate 33 (see FIG. 4) across the boundary of the different metal materials. Consequently, a phase delay of radiant energy that is radiated when the heat has returned to the surface becomes relatively large as represented by the curve X2B for radiant energy (return energy after internal heat transfer) radiated by a return of the heat after the internal heat transfer.

Figure 8:
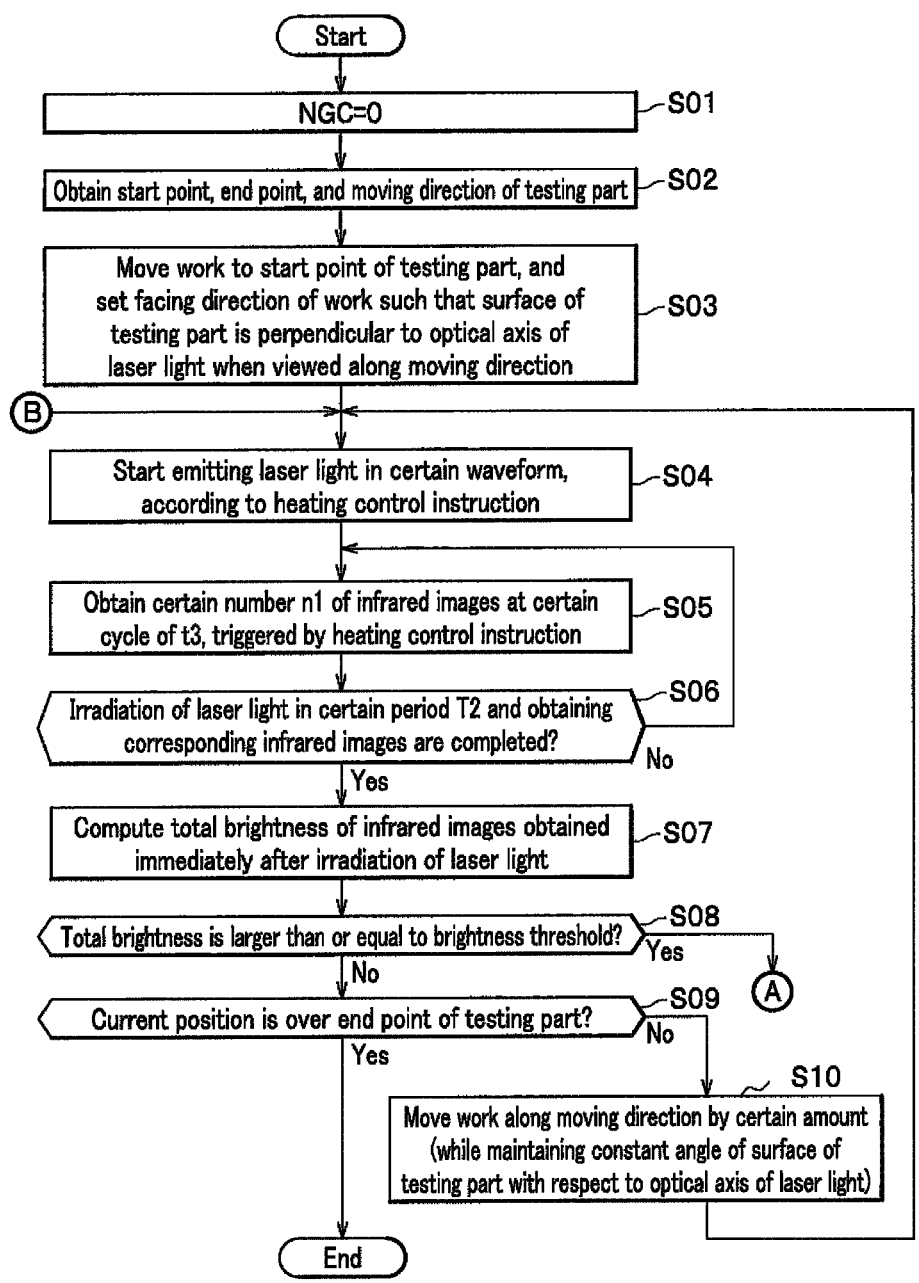
FIG. 8 is a flowchart showing the flow of control to change the setting of the surface angle of the lamination joining portion of a testing object by the data processing device, a testing system control device, and a controller.
Figure 9:
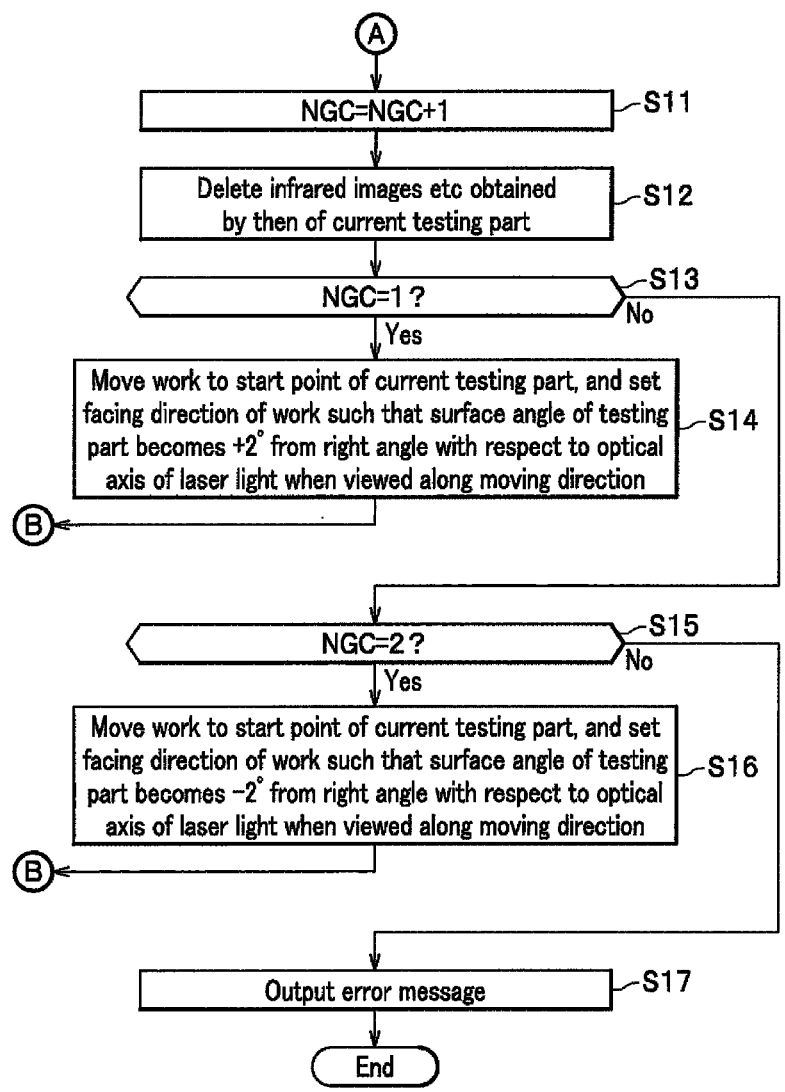
FIG. 9 is a flowchart continued from FIG. 8.

Referring to FIGS. 8 and 9, and referring to FIGS. 1, 5, 6A, 6B, 7A, 7B, 10A, and 10B, as appropriate, the flow of control of changing the setting of the surface angle of the lamination joining portion 35 of a testing object by the data processing device, the testing system control device, and the controller will be described below. FIGS. 8 and 9 are flowcharts showing the flow of control of changing the setting of the surface angle of the lamination joining portion of a testing object by the data processing device, the testing system control device, and the controller.

In step S01, the testing system control device 13 is set as NGC=0. NGC is a designation flag indicating which one of the above-described programs PA, PB, and PC is selected, wherein NGC=0 represents a case that the angle of the optical axis of a laser light 61 is set to a right angle when viewed along the moving direction of the testing part with respect to the surface of the testing part (a case of using the program PA); NGC=1 represents a case that the angle is set to +2° (a case of using the program PB); NGC=2 represents a case that the angle is set to −2° (a case of using the program PC); and NGC=3 represents a case that, by any one of NGC=0 to 2, the infrared intensity as the average value of the total infrared intensities (brightness) of respective infrared images in the number N1A of infrared images exceeds an intensity threshold and appropriate image capturing has been unsuccessful, the number N1A of infrared images having been obtained by setting such as to obtain infrared images in the initial period during the certain time delay ΔT, triggered by a heating control instruction output by the image processing control section 4a to the laser light control section 6 as a trigger signal.

In step S02, upon reception of designation NGC=0 from the testing system control device 13, the controller 11a reads out the program PA from the storage section of the controller 11a to obtain the start point, the end point, and the moving direction of the testing part.

In step S03, the controller 11a moves the work 1 to the start point of the testing part, and sets the facing direction of the work 1 to be at a right angle, perpendicular in other words, when viewed along the moving direction, with respect to the optical axis of the laser light 61.

In step S04, the image processing control section 4a of the data processing device 4 outputs a heating control instruction to the laser light control section 6, and the laser light irradiation section 2 and the laser light control section 6 start irradiation of (emitting) a laser light 61 in a certain waveform, according to the heating control instruction.

In step S05, based on the first image obtaining control instruction from the image processing control section 4a, the image obtaining section 4b obtains the certain number N1 of infrared images with the certain cycle T3, triggered by the heating control instruction. Concretely, the image obtaining section 4b obtains infrared images in the number N1 during the period T2 (see FIG. 7), triggered by the heating control instruction, and temporarily stores the infrared images in the number N1 in the memory of the image obtaining section 4b.

In step S06, the image processing control section 4a checks whether or not irradiation of the laser light 61 in a certain waveform in the certain period T2 and obtaining of infrared images corresponding to the irradiation are completed. If not completed yet (No), the process returns to step S05, and if completed (Yes), the process proceeds to step S07.

In step S07, the image processing control section 4a reads out the initial infrared images in the number N1A out of the temporarily stored certain number N1 of infrared images in the memory, and thereafter computes the total brightness of each infrared image by integrating the brightness of respective pixels of the each infrared image, and then computes the total brightness (infrared intensity) of the average infrared image of infrared images in the number N1A ('compute the total brightness of infrared images obtained immediately after the irradiation of laser light').

In step S08, the image processing control section 4a checks whether or not the total brightness is larger than or equal to a brightness threshold (intensity threshold). If the total brightness is larger than or equal to the brightness threshold (Yes), the image processing control section 4a outputs a determination result signal notifying this fact to the testing system control device 13 and the process proceeds to step S11 in FIG. 9, according to a connector (A), and if the total brightness is smaller than the brightness threshold (No), the process proceeds to step S09.

In step S09, the testing system control device 13 communicates with the controller 11a to check whether or not the current position is over the end point of the testing part. If the current position is over the end point of the testing part (Yes), testing of one testing part is terminated. If the current position is not over the end point of the testing part (No), the image processing control section 4a reads out infrared images in the certain number N1B from the memory of the image obtaining section 4b into the fast Fourier transform section 4c, and controls the fast Fourier transform section 4c to perform fast Fourier transform. Then, the process proceeds to step S10, and the controller 11a moves the work 1 along the moving direction by a certain amount. Herein, the angle of the surface of the testing part with respect to the optical axis of the laser light 61 is maintained constant, and the relative distances to the laser light irradiation section 2 and the infrared camera 3 are also maintained constant.

Figure 10A:
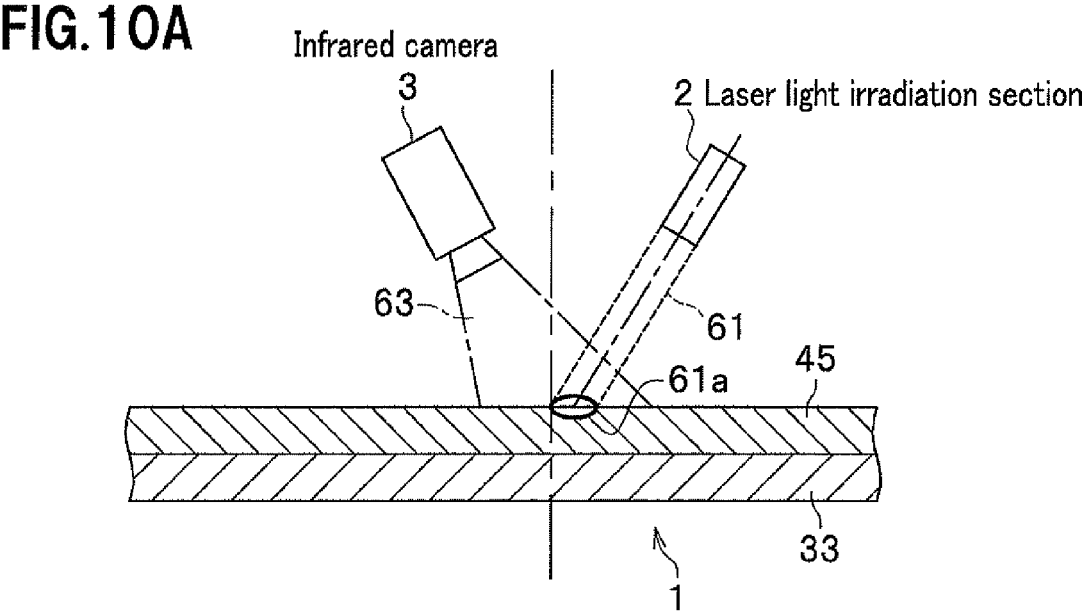
Figure 10B:
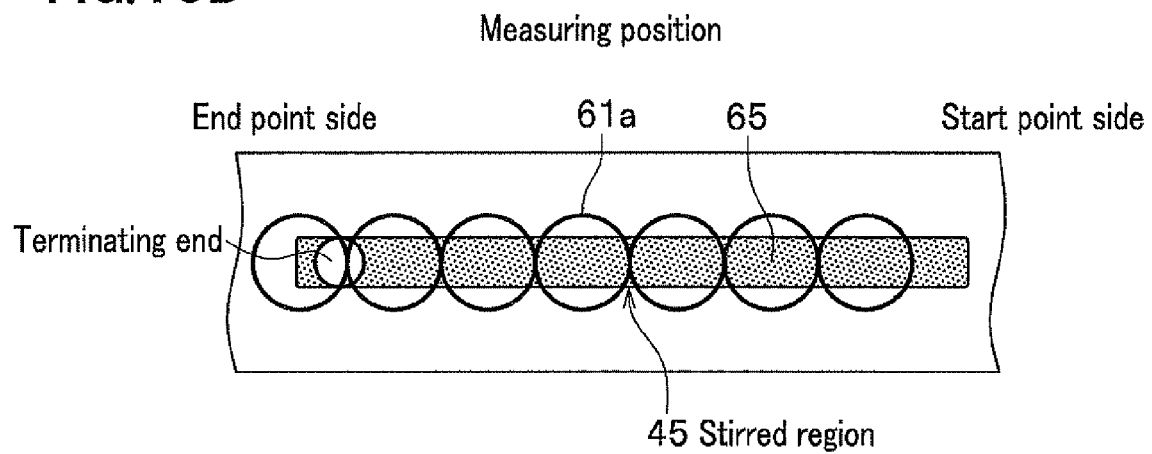

Incidentally, this movement by the certain amount is performed in a movement amount such that, as shown in FIG. 10B, the irradiated portion 61a by the laser light 61 is continuous without a gap therein so that the surface signature 65 of the lamination joining portion 35 can be continuously tested, or such that the irradiated portion 61a is partially overlapping therein along the moving direction.

In step S11, the testing system control device 13 increments the value of NGC by 1 as NGC=NGC+1 and inputs the value of NGC to the controller 11a.

In step S12, the image processing control section 4a deletes the infrared images of the current testing part obtained in Step S05 from the memory of the image obtaining section 4b. Further, the image processing control section 4a also deletes computation results of short-time Fourier transform, which have been computed by the fast Fourier transform section 4c on a series of testing portions (portions corresponding to the irradiated portion 61a) of the testing part and stored via a communication line in the storage section 5c of the console device 5, and further deletes the phase image of the testing part, which has been obtained by computation by the phase image computing section 5b, using the computation results of the short-time Fourier transform, and stored in the storage section 5c ('deletes infrared images of the testing part obtained by then'). It is convenient if a message notifying of this fact is displayed on the input section 51 of the console device 5. Further, it is convenient if a log record of having performed such processing is recorded into the storage section 5c.

In step S13, the controller 11a checks whether or not the value of the flag NGC having been input in step S11 from the testing system control device 13 is 1 ('NGC=1?'). If NGC=1 (Yes), the process proceeds to step S14, and if not (No), the process proceeds to step S15. In step S14, the controller 11a moves the work 1 to the start point of the current testing part, and sets the facing direction of the work 1 so that the angle of the testing part of the testing part becomes +2° from a right angle in a view along the moving direction (see FIG. 6B) with respect to the optical axis of laser light 61. That is, the controller 11a selects the program PB, moves the work 1 to the start point of the testing part, and sets the facing direction of the work 1 so that the angle of the testing part of the testing part becomes +2° from a right angle in a view along the moving direction (see FIG. 6B) with respect to the optical axis of laser light 61. Then, the process returns to step S04 in FIG. 8, according to a connector (B).

In step S15, the controller 11a checks whether or not the value of the flag NGC having been input in step S11 from the testing system control device 13 is 2 ('NGC=2?'). If NGC=2 (Yes), the process proceeds to step S16, and if not (No), the process proceeds to step S17. In step S16, the controller 11a moves the work 1 to the start point of the current testing part, and sets the facing direction of the work 1 so that the angle of the testing part of the testing part becomes −2° from a right angle in a view along the moving direction (see FIG. 6B) with respect to the optical axis of laser light 61. That is, the controller 11a selects the program PC, moves the work 1 to the start point of the testing part, and sets the facing direction of the work 1 so that the angle of the testing part of the testing part becomes −2° from a right angle in a view along the moving direction (see FIG. 6B) with respect to the optical axis of laser light 61. Then, the process returns to step S04 in FIG. 8, according to a connector (B).

When the process proceeds to step S17 with No in step S15, the controller 11a outputs an error message via the testing system control device 13 to the display section 52 of the console device 5 and stops testing.

As described above, according to the present embodiment, even in case that the testing part of the lamination joining portion 35 is in the vicinity of the vertical wall 31b of the flange portion 1a (see FIG. 6A), when the temporal transitions of radiant energy from the surfaces of the respective testing portions of the testing part by surface heating with laser light 61 from the laser light irradiation section 2 are obtained as infrared images with the certain cycle T3 by the infrared camera 3 by using a non-destructive method by infrared way lock-in thermography, it is possible to incline the work 1 such as to decrease the above-described 'noise, on an infrared image, caused by reflection on a vertical wall in the vicinity of the testing part'. As a result, while maintaining the distances of the surface of the testing part relative to the laser light irradiation section 2 and the infrared camera 3 to be constant at respective certain values, it is possible to finely adjust the angle between the optical axis of the laser light 61 and the surface of testing part in a view along the moving direction and thereby decrease the above-described 'noise, on an infrared image, caused by reflection on a vertical wall in the vicinity of the testing part', which enables accurate determination of effectiveness/defectiveness of joining of the lamination joining portion 35 by friction stir welding.

Further, as programs for holding a work 1 to finely adjust the angle between the optical axis of laser light 61 and the surface of a testing part in testing, by creating and registering in advance, in the controller 11a, the programs (program PB, program PC) for which the angle between the optical axis of laser light 61 and the surface of the testing part in a view along the moving direction of the testing part is set to be a plus and a minus value (respectively for the program PB and the program PC) by a certain value, compared with a right angle for the program (program A), it is possible to perform non-destructive testing, easily switching a program, so as to eliminate time loss caused by returning to a testing process or tuning a testing program of the handling robot 11 each time, and efficient and accurate testing is thereby realized.

FIGS. 10A and 10B are schematic illustrations of application of the laser light to the surface of a lamination joining portion formed by friction stir welding and obtaining infrared images, wherein FIG. 10A is a schematic illustration of the lamination joining portion viewed from a right angle side direction with respect to the longitudinal direction of the lamination joining portion, and FIG. 10B is a schematic lustration of moving an irradiated portion onto which laser light is applied for non-destructive testing wherein the surface of the lamination joining portion is viewed from the above.

Herein, movement of the irradiated portion 61a with laser light 61 along the surface signature 65 of the stirred region 45 of the lamination joining portion 35 for non-destructive testing is not shown such as to be continuous with partial overlapping. In case that the lamination joining portion 35 is long enough, such testing is possible, however, in case that the lamination joining portion 35 is short, it is desired that the irradiated portion 61a with the laser light 61 is formed such as to be continuous with partial overlapping in a point of view of ensuring a joining strength. Incidentally, 'the start point side' in FIG. 10B refers to the starting side of friction stir welding, and 'the end point side' refers to the terminating end side of friction stir welding.

In FIG. 10A, the laser light 61 from the laser light irradiation section 2 is schematically shown such that the laser light 61 is not necessarily perpendicularly applied to the surface signature 65 (see FIG. 10B) of friction stir welding, however, the work 1 is set such that the laser light 61 is applied perpendicularly to the work 1, at −2° from the perpendicular angle, or at +2° from the perpendicular angle.

With such an arrangement, improvement in the efficiency of non-destructive testing of the lamination joining portion 35 can be attained, and in case that laser light 61 is applied to the respective testing portions of a testing part in a narrow region, such as the flange portion 1a (see FIG. 3) of the work 1, it is also advantageous in preventing disturbance of accurate measurement of radiant energy from the surface of a testing portion by the infrared camera 3, wherein the disturbance could occur if laser light 61 were applied to a part other than the testing part.

Incidentally, the infrared camera 3 in FIGS. 1, 2, 5, and 10A, the infrared camera 3 is shown schematically such that the infrared camera 3 obliquely captures an image of the surface of the testing part, however, capturing an image of the surface of the testing part such that the optical axis is in a direction close to the optical axis of the laser light irradiation section 2 and in a direction as close as possible to the direction perpendicular to the surface of the testing part is appropriate for accurate measurement of radiant energy radiated from the surface of the testing part by infrared images.

Further, the optical system of the laser light irradiation section 2 has a shape, in a plan view from the above of the irradiated portion 61a with the laser light 61, that covers the lateral direction of the surface signature 65 and is, for example, a circular shape.

Further, the view angle 63 (see FIG. 10A) of the infrared camera 3 is preferably set to have a visual field, for capturing an image, with a range wide enough and wider than the irradiated portion 61a.

FIGS. 11A and 11B are illustrations of examples of effectiveness/defectiveness of joining by phase images, wherein FIG. 11A is an illustration of examples of phase images of testing objects on which determination of effective joining has been made (effective products, passed products), and FIG. 11B is an illustration of examples of phase images of testing objects on which determination of defective joining has been made (defective products). As shown in FIG. 11A as colored original images, the effective products shows, in the figure, colors of white, yellow, red, and orange at the central portion, along the upper/lower width direction, of the irradiated portion 61a irradiated with laser light 61, wherein these colors represent effective metal joining. On the other hand, the defective products includes, in the figure, a blue looking region in colors of green and blue at the central portion, along the upper/lower width direction, of the irradiated portion 61a irradiated with laser light 61, wherein these colors represent defective metal joining.

Figure 12A:
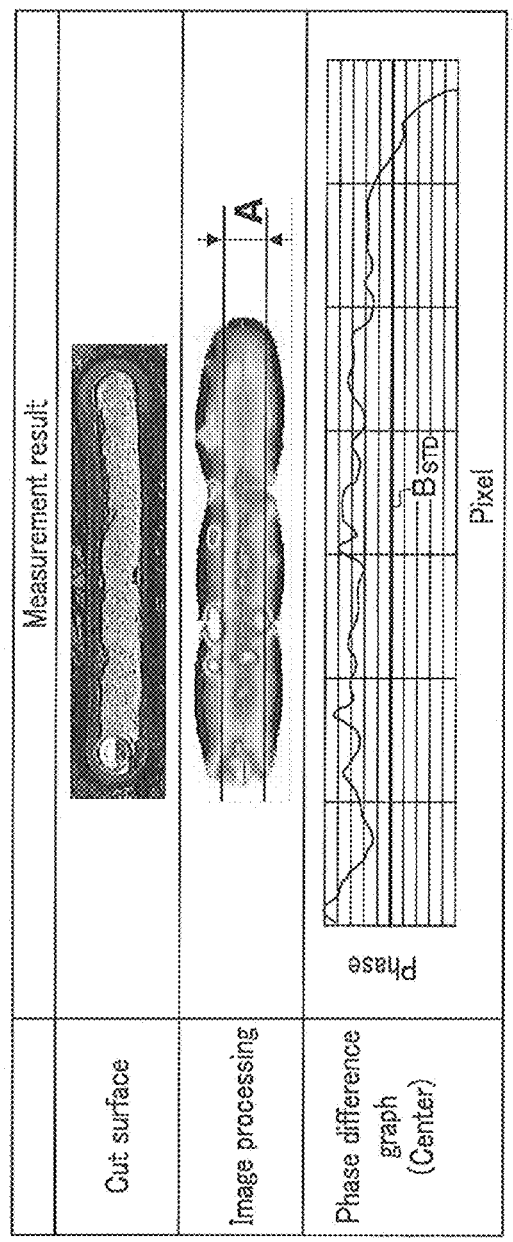
Figure 12B:
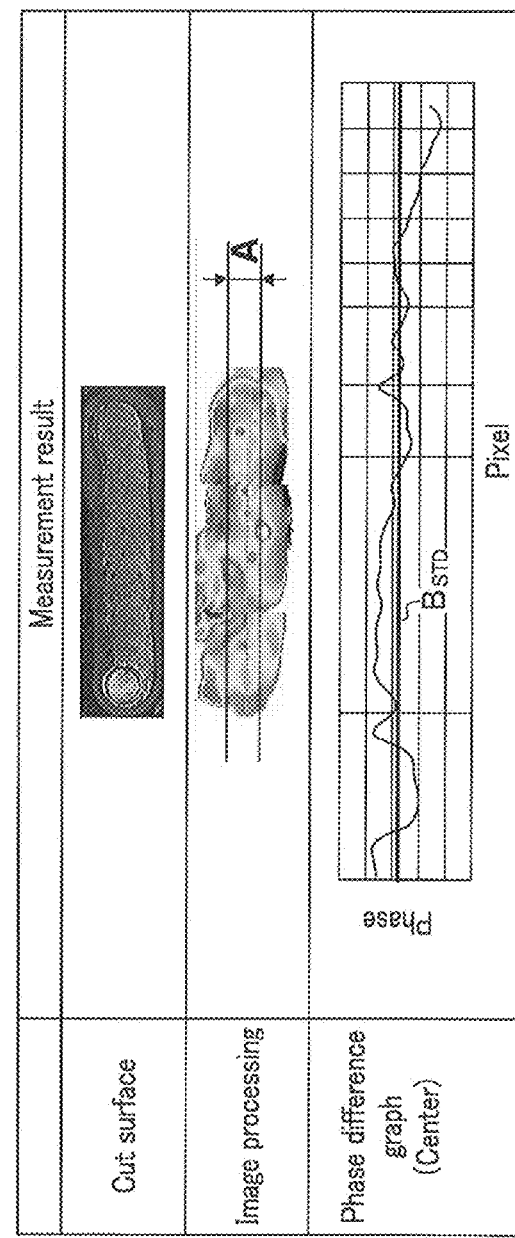

FIGS. 12A and 12B are illustrations of examples of effectiveness/defectiveness determination on lamination joining portions by phase images in a different manner, wherein FIG. 12A shows an example in case of determination of effective joining, the upper section being a plan-view photograph of the cut surface at a joining boundary on which effective joining has been confirmed, the middle section being an illustration of an example of a phase image in case of effective joining, and the lower section being an illustration of an example of phase difference in a phase image of a lamination joining portion in the plan lateral direction, for example, at the center, and FIG. 12B shows an example in case of determination of defective joining, the upper section being a plan photograph of the cut surface at a joining boundary on which defective joining has been confirmed, the middle section being an illustration of an example of a phase image in case of defective joining, and the lower section being an illustration of an example of phase difference in a phase image of a lamination joining portion in the plan lateral direction, for example, substantially at the center.

The cut surface of a colored original image in the upper section of the FIG. 12A shows observation of the surface state obtained by cutting the boundary surface of metal joining, wherein the bead surface is glossy. In contrast, the cut surface of a colored original image in the upper section of the FIG. 12B shows observation of the surface state obtained by cutting the boundary surface of metal joining, wherein the bead surface is not glossy but dark.

In the phase image of the colored original image subjected to image processing, shown in the middle section of FIG. 12A, the joining boundary surface 45a (see FIG. 4) has colors of white, red, orange, and yellow in a width A, wherein these colors represent effective metal joining. The graph shown in the lower section of FIG. 12A represents, by a numeric value, the phase delay of each pixel at the center with respect to the upper/lower direction of the width A in the middle section of FIG. 12A. In the graph in the lower section of FIG. 12A shows that the upper a position is along the vertical axis, the smaller the phase delay is, and the lower a position is along the vertical axis, the larger the phase delay is. As represented by the thin line of this graph, regarding the phase delays of the respective pixels, it is recognized that a phase delay is smaller, for example, at the center with respect to the upper/lower direction of the width A, than a phase delay (a certain determination value) $B_{STD}$ as determination criterion, and is thus recognized that effective metal joining can be numerically determined easily.

In the phase image of the colored original image subjected to image processing, shown in the middle section of FIG. 12B, the width A of the joining boundary surface 45a (see FIG. 4) includes a blue looking portion in colors green and blue without showing effective metal joining. The graph shown in the lower section of FIG. 12B represents, by a numeric value, the phase delay of each pixel, for example, approximately at the center with respect to the upper/lower direction of the width A in the middle section of FIG. 12B. As represented by the thin line of this graph, regarding the phase delays of the respective pixels, it is recognized that a phase delay is larger, for example, approximately at the center with respect to the upper/lower direction of the width A, than the phase delay $B_{STD}$ as determination criterion, and is thus recognized that a portion where effective metal joining is not made can be numerically determined easily.

In the lower sections of FIGS. 12A and 12B, an example is shown, for example, for a pixel row at the central position with respect to the upper/lower direction of the width A, however, by showing an example also for another pixel row along the upper/lower direction of the width A in the middle section, effectiveness/defectiveness of metal joining between different metal materials can be easily determined on the joining boundary surface 45a by a phase image.

Incidentally, whether or not a period T2 and a frequency ω having been set and a phase delay $B_{STD}$, which is determination criterion of a phase image obtained based on the period T2 and the frequency ω, are appropriate for a sample made by lamination joining by friction stir welding is confirmed by testing a cut surface in advance. Thus, it is guaranteed that accurate testing can be performed by non-destructive testing by the infrared lock-in thermography in the present embodiment.

As a method of determining effectiveness/defectiveness of a lamination joining portion 35, examples have been taken, as shown in FIGS. 12A and 12B, where the phase delay of each pixel on a line, along the longitudinal direction of the lamination joining portion 35, at a specific position with respect to the lateral direction of the width A of the lamination joining portion 35 in a phase image of the lamination joining portion 35 is compared with a phase delay $B_{STD}$ as a determination criterion, however, the method is not limited thereto.

An arrangement may be made such as to compute, in the width A of the lamination joining portion 35, the average phase delay of all pixels included in a rectangle with a certain length along the longitudinal direction, for example, a length of LB, based on a phase image, and determine that effective metal joining is not made if the value of the average phase delay is larger than the value of the average phase delay of a determination criterion.

Incidentally, the length along the lateral direction of the rectangular lamination joining portion 35 for computing the value of average phase delay is not limited to the width A of the lamination joining portion 35, and, a plurality of rectangles with a smaller length may be set along the direction of width A of the lamination joining portion 35 to compute the average phase delays of the respective rectangles for determination of effectiveness/defectiveness of metal joining.

Or, an arrangement may be made such that, a region with a certain length along the longitudinal direction of the lamination joining portion 35 and with the width A of the lamination joining portion 35 is set as a color map; the ratio of the number of pixels in a blue looking region, which is included in the above-described region and includes colors of green and blue, to the number of pixels included in the above-set region is determined; and defective joining is determined if the ratio is larger than the value of a ratio of determination criterion. In this case, the shape of the above-set region is not limited to a rectangle but may be a shape of region along a shape having been set in advance in the longitudinal direction of the lamination joining portion 35.

In the present embodiment, although the aluminum alloy member 31 and the steel plate 33 have been described as an example of different metal materials, different metal materials are not limited thereto.

Further, in the present embodiment, arrangement has been made such that, based on a series of task instructions having been input in advance to the controller 11a, the testing system control device 13 controls the handling robot 11 to repeat a testing task in a certain preset order, wherein the testing task is such as 'fix the positions and angles of a testing portion of a testing part respectively relative to the laser light irradiation section 2 and the infrared camera 3 and perform testing'→'move the testing part by a certain amount of movement'→'fix the position and the angle of the next testing portion of the testing part', however arrangement is not limited thereto. As shown in FIGS. 1 and 2, arrangement may be made such as to dispose monitoring cameras 15A, 15B and input camera video images by these cameras to the testing system control device 13. In this case, the testing system control device 13 reads, by the monitoring cameras 15A and 15B, identification information indicated or marked on the surface of a work 1 gripped by the handling robot 11, and identifies a work 1 being a testing object to input the work 1 to the console device 5.

Further, arrangement may be made such that the testing system control device 13 detects a surface signature 65 of the testing part of the work 1 by the camera images from the monitoring cameras 15A and 15B, distinguishing the surface signature 65 from a surface that is not of the lamination joining portion 35 of the aluminum alloy member 31; and corresponding to the tolerance of the testing part, the positions relative to the laser light irradiation section 2 and the infrared camera 3 are adjusted from a position that is obtained by a series of task instructions having been input in advance. Incidentally, in order to detect the distance and angle of a work 1, if at least two monitoring cameras 15A and 15B are prepared, a known program for camera image recognition can easily detect the distance and the angle of the work 1 by triangulation.

Modification

In the present embodiment, the fast Fourier transform section 4c reads out infrared images, with a cycle T3 and of N1B times, temporarily stored in the image obtaining section 4b, and a result of performing the short-time Fourier transform on the brightness of each pixel is stored in the storage area for short-time Fourier transform result of the storage section 5c of the console device 5, however, the invention is not limited thereto.

Instead of irradiating with laser light in the above-described certain waveform onto each testing portion of a testing part only once, laser light may be applied N2 times with a cycle of the period T2 (refer to irradiation with laser light in a rectangular wave with a temporal width of T1 represented by virtual lines in FIG. 7). In this case, out of 'N1×N2' infrared images temporarily stored in the image obtaining section 4b, the image processing control section 4a first reads out initial 'certain N1A×N2' infrared images in the period T2; integrates the brightnesses of the pixels of each of the 'N1A×N2' infrared images to compute the brightness of each one entire infrared image; then computes the averaged total brightness of 'N1A×N2' images; and, in step S08, uses the total brightness to check whether the total brightness is larger than or equal to a brightness threshold (strength threshold).

Then, in step S08, if the total brightness is smaller than the brightness threshold (intensity threshold), the image processing control section 4a controls the fast Fourier transform section 4c to read out the infrared images of 'N1B×N2' times temporarily stored in the image obtaining section 4b, performs average processing of the digital values of the brightnesses of the respective pixels of infrared images, which have been obtained at the same timing after the certain temporal delay of ΔT, for a certain preset region of the 'N1B×N2' infrared images, the infrared images having been obtained in response to irradiation with the laser light of N2 times, and then creates N1B infrared images with the certain cycle T3.

Then, the fast Fourier transform section 4c performs computation of fast Fourier transform of the short-time Fourier transform pixel by pixel of the integrated and averaged certain number NB1 of infrared images between the certain number N1B of infrared images, and stores a result of performing the short-time Fourier transform of the brightness of each pixel in the storage area for short-time Fourier transform result of the storage section 5c of the console device 5. Then, the fast Fourier transform section 4c notifies via the image processing control section 4a to the control section 5a that the above-described computation of the short-time Fourier transform is completed.

In such a manner, infrared images are obtained by irradiating with laser light N2 times with the cycle of the period T2, infrared images are created as integrated average corresponding to N1B times of the same timing from the number of 'N1B×N2' of images, and then a phase image is created. Thus, noise can be reduced and an accurate phase image can be obtained.

Further, fast Fourier transform computation of the short-time Fourier transform by the fast Fourier transform section 4c may be performed on the above-described specific frequency ω. That is, the fast Fourier transform section 4c in the present embodiment does not perform frequency analysis, such as an ordinary short-time Fourier transform, but performs computation processing for analysis of phase (phase of infrared light) with respect to the temporal transition of the brightness (the amount of infrared light) of each pixel for the specific frequency ω. Thus, the time for Fourier transform can be reduced.

As described above, there is provided a non-destructive testing system, using infrared lock-in thermography, comprising:

a testing object handling device that transports and grips a testing object;

a testing position control unit that controls the testing object handling device and thereby sets the surface of the lamination joining portion of the testing object to certain positions and certain directions respectively relative to the heating light irradiation source and the infrared camera;

a heating control unit that controls projection of heating light from the heating light irradiation source to perform heating of a surface on one side of a lamination joining portion of different metal materials from a heating light irradiation source, the heating being in a certain preset waveform;

an infrared image obtaining unit that obtains the infrared images from radiant energy from the surface on the one side at a certain cycle with the infrared camera;

a phase image obtaining unit that obtains an amount and a phase of infrared light by computation processing, based on brightness of each unit pixel of the obtained infrared images, and further creates a phase image; and an effectiveness-defectiveness determining unit that, based on the obtained phase image, determines whether or not a region with a phase delay larger than a certain preset determination value is present in the lamination joining portion to determine whether joining of the different metal materials is effective or defective, wherein when infrared intensity of an infrared image obtained in an initial period of the heating out of the infrared images obtained, based on the heating in the certain preset waveform, by the infrared image obtaining unit via the infrared camera exceeds a predetermined intensity threshold, the testing position control unit adjusts the direction of the lamination joining portion while maintaining the certain positions of the surface of the lamination joining portion respectively relative to the heating light irradiation source and the infrared camera, and thereafter, the heating control unit again projects the heating light so that the infrared image obtaining unit again obtains infrared images.

What is claimed is:

1. A non-destructive testing system using a non-destructive testing method by infrared lock-in thermography, wherein the non-destructive testing method:

performs heating of a surface on one side of a lamination joining portion of different metal materials from a heating light irradiation source, the heating being in a certain preset waveform;

obtains infrared images from radiant energy from the surface on the one side, the radiant energy being caused by the heating in the certain waveform, the infrared images being obtained with a certain cycle by an infrared camera;

obtains an amount and a phase of infrared light by computation processing, based on brightness of each unit pixel of the obtained infrared images; and determines whether joining of the different metal materials is effective or defective, the non-destructive testing system comprising:

a testing object handling device that transports and grips a testing object;

a testing position control unit that controls the testing object handling device and thereby sets the surface of the lamination joining portion of the testing object to certain positions and certain directions respectively relative to the heating light irradiation source and the infrared camera;

a heating control unit that controls irradiation with heating light from the heating light irradiation source;

an infrared image obtaining unit that obtains the infrared images obtained by the infrared camera, based on heating in the certain preset waveform from the heating control unit;

a phase image obtaining unit that obtains an amount and a phase of infrared light by computation processing, based on brightness of each unit pixel of the obtained infrared images, and further creates a phase image; and an effectiveness/defectiveness determining unit that, based on the obtained phase image, determines whether or not a region with a phase delay larger than a certain preset determination value is present in the lamination joining portion, wherein when infrared intensity of an infrared image obtained in an initial period of the heating out of the infrared images obtained, based on the heating in the certain preset waveform, by the infrared image obtaining unit via the infrared camera exceeds a predetermined intensity threshold, the testing position control unit adjusts the direction of the lamination joining portion while maintaining the certain positions of the surface of the lamination joining portion respectively relative to the heating light irradiation source and the infrared camera, and thereafter, the heating control unit again performs irradiation with the heating light so that the infrared image obtaining unit again obtains infrared images;

wherein the region with a phase delay is a representation of phase delays of the respective pixels of the infrared images; and wherein the phase delay is a numeric value determined by performing computation processing for analysis of the phase of infrared light with respect to a temporal transition of the brightness of each pixel of the infrared images for a specific frequency.

2. The non-destructive testing system according to claim 1, wherein the testing object has a structure having a vertical wall in a vicinity of the lamination joining portion and a possibility that the radiant energy from the surface on the one side of the lamination joining portion reflects on the vertical wall to thereby enter the infrared camera, the radiant energy having been caused by the heating of the surface on the one side of the lamination joining portion by the heating light irradiation source.

3. The non-destructive testing system according to claim 1, wherein the testing object has a structure having a vertical wall in a vicinity of the lamination joining portion and a possibility that the heating light from the heating light irradiation source onto the surface on the one side of the lamination joining portion reflects on the vertical wall to thereby enter the surface on the one side of the lamination joining portion.

4. The non-destructive testing system according to claim 1, wherein the testing position control unit stores in advance a plurality of testing part scanning programs for adjusting only the certain directions of the surface of the lamination joining portion while maintaining the certain positions, the certain directions and the certain positions being respectively relative to the heating light irradiating source and the infrared camera, wherein when infrared intensity of an infrared image obtained in the initial period of the heating out of the infrared images obtained by the infrared camera, the obtaining being triggered by a timing of heating in the preset waveform, exceeds a predetermined intensity threshold, the testing position control unit switches the plurality of testing part scanning programs stored in advance to thereby adjust only the certain directions of the surface of the lamination joining portion respectively relative to the heating light irradiating source and the infrared camera while maintaining the certain relative positions, and wherein the heating control unit thereafter again performs irradiation with the heating light so that the infrared image obtaining unit again obtains infrared images.

5. The non-destructive testing system according to claim 2, wherein the testing position control unit stores in advance a plurality of testing part scanning programs for adjusting only the certain directions of the surface of the lamination joining portion while maintaining the certain positions, the certain directions and the certain positions being respectively relative to the heating light irradiating source and the infrared camera, wherein when infrared intensity of an infrared image obtained in the initial period of the heating out of the infrared images obtained by the infrared camera, the obtaining being triggered by a timing of heating in the preset waveform, exceeds a predetermined intensity threshold, the testing position control unit switches the plurality of testing part scanning programs stored in advance to thereby adjust only the certain directions of the surface of the lamination joining portion respectively relative to the heating light irradiating source and the infrared camera while maintaining the certain relative positions, and wherein the heating control unit thereafter again performs irradiation with the heating light so that the infrared image obtaining unit again obtains infrared images.

6. The non-destructive testing system according to claim 3, wherein the testing position control unit stores in advance a plurality of testing part scanning programs for adjusting only the certain directions of the surface of the lamination joining portion while maintaining the certain positions, the certain directions and the certain positions being respectively relative to the heating light irradiating source and the infrared camera, wherein when infrared intensity of an infrared image obtained in the initial period of the heating out of the infrared images obtained by the infrared camera, the obtaining being triggered by a timing of heating in the preset waveform, exceeds a predetermined intensity threshold, the testing position control unit switches the plurality of testing part scanning programs stored in advance to thereby adjust only the certain directions of the surface of the lamination joining portion respectively relative to the heating light irradiating source and the infrared camera while maintaining the certain relative positions, and wherein the heating control unit thereafter again performs irradiation with the heating light so that the infrared image obtaining unit again obtains infrared images.

* * * * *